US012465236B2

(12) United States Patent
Wagner et al.

(10) Patent No.: US 12,465,236 B2
(45) Date of Patent: Nov. 11, 2025

(54) AIRFLOW DEVICES FOR MAGNETIC RESONANCE IMAGING

(71) Applicant: CANON MEDICAL SYSTEMS CORPORATION, Tochigi (JP)

(72) Inventors: Jennifer Wagner, Lyndhurst, OH (US); Yoshinori Hamamura, Moreland Hills, OH (US); Michael Steckner, Beachwood, OH (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 301 days.

(21) Appl. No.: 18/320,835

(22) Filed: May 19, 2023

(65) Prior Publication Data

US 2024/0382100 A1 Nov. 21, 2024

(51) Int. Cl.

*A61B 5/055* (2006.01)
*A47C 21/04* (2006.01)
*A61B 6/00* (2024.01)

(52) U.S. Cl.

CPC ............ *A61B 5/055* (2013.01); *A47C 21/044* (2013.01); *A61B 6/4405* (2013.01)

(58) Field of Classification Search

CPC ........... A63F 2003/00236; A61B 5/055; A61B 6/4405; A61B 5/702; A61B 5/704; A61B 2090/374; A61B 3/0083; A61B 6/4488; A61B 8/40; A47C 21/044; A47C 27/088; A61F 7/08; A61F 2007/0056; A47D 15/008

(Continued)

(56) References Cited

U.S. PATENT DOCUMENTS 3,938,205 A * 2/1976 Spann .................. A47C 20/027 5/632
4,233,700 A * 11/1980 Spann .................. A47C 20/027 5/632

(Continued)

FOREIGN PATENT DOCUMENTS

CN 215304470 U 12/2021
EP 2538912 B1 * 1/2017 ............... A61F 7/00

(Continued)

OTHER PUBLICATIONS

Cutters REV Impact 5Pad Shirt Black, downloaded from https://www.forelle.com/american-football/protection-medical/padded-shirts/cutters-rev-impact-5pad-shirt-black/18127/ on Oct. 2022.

(Continued)

*Primary Examiner* — David R Hare
*Assistant Examiner* — George Samuel Gines
(74) *Attorney, Agent, or Firm* — Canon U.S.A., Inc. IP Division

(57) ABSTRACT

According to some embodiments, a device comprises a body and one or more breathable barriers. The body includes a plurality of openings and forms one or more air spaces therein, wherein the plurality of openings and the one or more air spaces allow air to flow through the body in at least two directions, and wherein the at least two directions are orthogonal to each other. The one or more breathable barriers are positioned over at least some of the plurality of openings, wherein the one or more breathable barriers allow air to flow through the at least some of the plurality of openings into the one or more air spaces.

21 Claims, 21 Drawing Sheets

(58) Field of Classification Search
USPC .................................................... 5/652.1, 601
See application file for complete search history.

(56) References Cited

U.S. PATENT DOCUMENTS

| | | | | |
|---|---|---|---|---|
| 4,502,658 | A * | 3/1985 | Wirt | A63F 3/0625 248/452 |
| 5,683,441 | A | 11/1997 | Dickerhoff et al. | |
| 5,697,113 | A * | 12/1997 | Shatz | A47C 21/046 5/655 |
| 6,092,248 | A | 7/2000 | Boemmel et al. | |
| 6,371,976 | B1 | 4/2002 | Vrzalik et al. | |
| 6,641,521 | B2 | 11/2003 | Kolarovic | |
| 6,764,502 | B2 | 7/2004 | Bieberich | |
| 7,681,262 | B2 * | 3/2010 | Weedling | A47C 20/027 5/655.3 |
| 7,712,164 | B2 * | 5/2010 | Chambers | A61G 7/05784 607/104 |
| 8,147,396 | B2 | 4/2012 | Srinivasan | |
| 9,131,871 | B2 | 9/2015 | Boersma et al. | |
| 9,314,118 | B2 * | 4/2016 | Blazar | A47G 9/1027 |
| 9,462,984 | B2 | 10/2016 | Gregerson et al. | |
| 2004/0062910 | A1 | 4/2004 | Morrison | |
| 2009/0100602 | A1 * | 4/2009 | Rathie | A47G 9/10 5/655 |
| 2014/0249401 | A1 * | 9/2014 | Van Den Brink | A61F 7/10 600/410 |
| 2016/0166092 | A1 * | 6/2016 | Alletto, Jr. | A47G 9/1036 5/636 |
| 2018/0140101 | A1 * | 5/2018 | Davis | A47C 7/746 |
| 2021/0030174 | A1 * | 2/2021 | Romo | A47G 9/1081 |
| 2022/0087625 | A1 * | 3/2022 | Keller | A61B 6/4488 |

FOREIGN PATENT DOCUMENTS

| | | | |
|---|---|---|---|
| EP | 3431059 | A1 | 1/2019 |
| WO | 2010/049100 | A1 | 5/2010 |
| WO | 2016/160111 | A1 | 10/2016 |

OTHER PUBLICATIONS

UMass Extension Greenhouse Crops and Floriculture Program, Fan and Pad Evaporative Cooling Systems, downloaded from https://ag.umass.edu/greenhouse-floriculture/fact-sheets/fan-pad-evaporative-cooling-systems on Mar. 31, 2023.

ClinicalTrials.gov, Evaluation of a Novel Patient Warming System during MRI, downloaded from https://clinicaltrials.gov/ct2/show/NCT03150953, Mar. 2019.

Evaporative Air Cooler with 3D Cooling Pad, downloaded from https://www.frysfood.com/p/evaporative-air-cooler-with-3d-cooling-pad/0081001268543?fulfillment=Pickup on Mar. 31, 2023.

MRI-Safe ConRad Thermal Blanket, Avante Health Solutions, downloaded Mar. 2023.

* cited by examiner

AIRFLOW DEVICES FOR MAGNETIC RESONANCE IMAGING

FIELD

This application generally concerns devices that are used in magnetic resonance imaging (MRI) for padding and for positioning patients.

BACKGROUND

MRI is an imaging modality that uses magnetic fields and radio frequency (RF) energy to create images of the interior of an object (e.g., a human) without using X-rays or other ionizing radiation. Patient-positioning devices are used to position patients during an MRI procedure and to improve patient comfort. Patient-positioning devices can both hold a patient in a particular position and increase the comfort of the patient during the imaging procedure.

DETAILED DESCRIPTION

Figure 1:
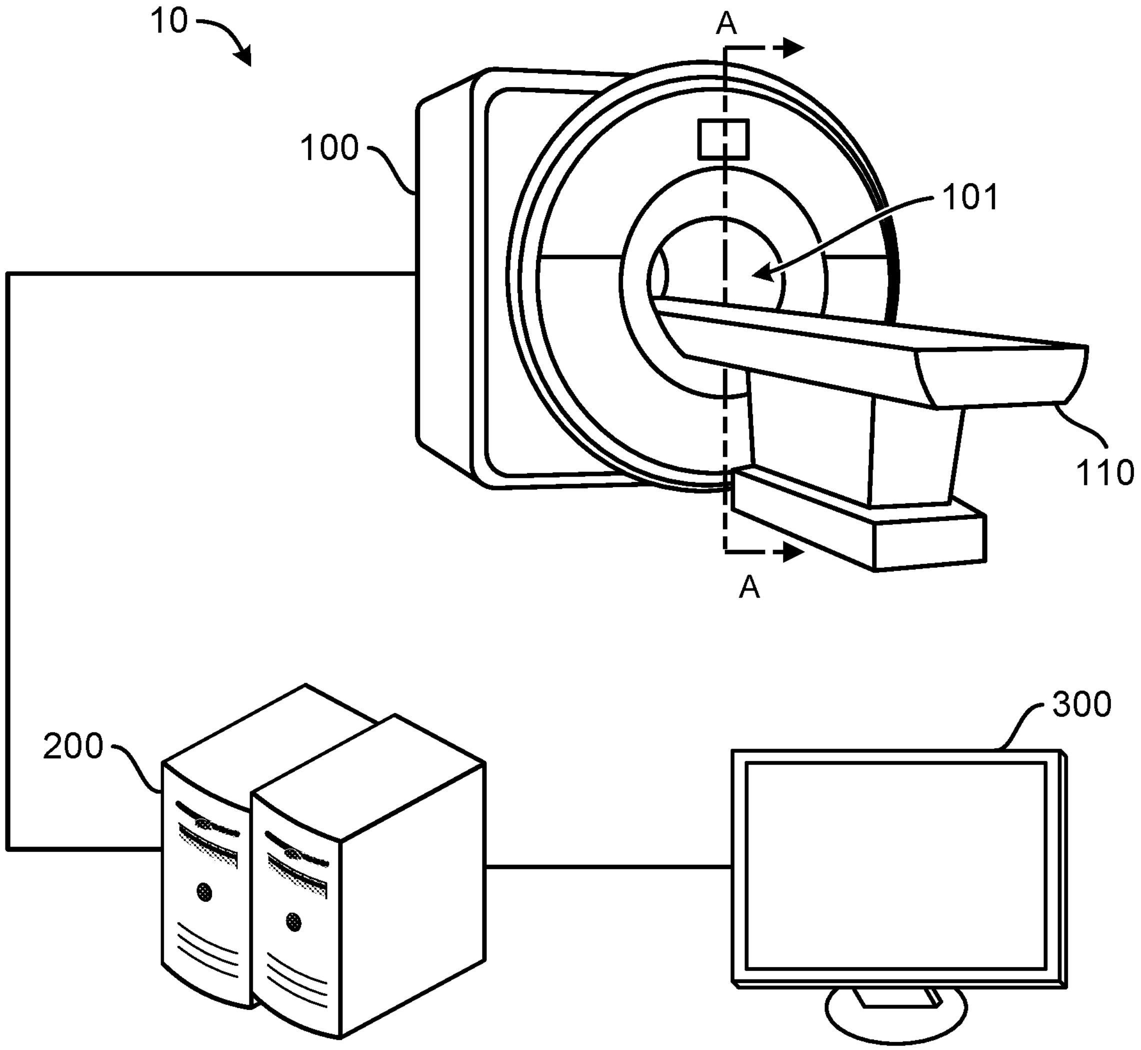
FIG. 1 illustrates an example embodiment of a medical-imaging system.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein. Furthermore, some embodiments include features from two or more of the following explanatory embodiments. Thus, features from various embodiments may be combined and substituted as appropriate.

As used herein, the conjunction "or" generally refers to an inclusive "or," although "or" may refer to an exclusive "or" if expressly indicated or if the context indicates that the "or" must be an exclusive "or." Also, as used herein, the terms "first," "second," and so on, do not necessarily denote any ordinal, sequential, or priority relation and may be used to more clearly distinguish one member, operation, element, group, collection, set, etc. from another without expressing any ordinal, sequential, or priority relation.

And in the following description and in the drawings, like reference numerals designate identical or corresponding members throughout the several views. Furthermore, an alphabetic suffix on reference numerals may be used to indicate a specific instance of the feature identified by the reference numerals. For example, the frames in a group of frames may be identified with the reference numerals 411 when a particular frame is not being distinguished. However, 411A may be used to identify a specific frame when the specific frame is being distinguished from the rest of the frames 411.

Additionally, some embodiments are set forth in the following paragraphs:

(1) A device comprising a body that includes a plurality of openings and that forms one or more air spaces therein, wherein the plurality of openings and the one or more air spaces allow air to flow through the body in at least two directions, and wherein the at least two directions are orthogonal to each other; and one or more breathable barriers positioned over at least some of the plurality of openings, wherein the one or more breathable barriers allow air to flow through the at least some of the plurality of openings into the one or more air spaces.

(2) The device of (1), wherein each air space of the one or more air spaces is in direct or indirect fluid communication with each opening of the plurality of openings.

(3) The device of (1), wherein the one or more air spaces allow air that passed through an opening, of the plurality of openings, in a first surface of the body to mix with air that entered through an opening, of the plurality of openings, in a second surface of the body that is orthogonal to the first surface.

(4) The device of (1), wherein the one or more breathable barriers are also waterproof.

(5) The device of (1), wherein the one or more breathable barriers are one or more breathable panels.

(6) The device of (1), wherein the body is inflatable.

(7) The device of (1), wherein the body is composed of open-cell foam.

(8) The device of (1), wherein the body includes two or more frames that are joined by one or more hinges, wherein the two or more frames can be swiveled on the one or more hinges to move the two or more frames between an unfolded configuration and a folded configuration, and wherein the two or more frames form the one or more air spaces while the two or more frames are in the folded configuration.

(9) A device comprising a body that includes a plurality of openings and that forms one or more air spaces therein, wherein the plurality of openings and the one or more air spaces allow air to flow through the body in at least two directions, and wherein the at least two directions are orthogonal to each other; and a casing that is configured to enclose the body, wherein the casing is breathable, and wherein, when the casing encloses the body, the casing allows air to flow through the plurality of openings into the one or more air spaces.

(10) The device of (9), wherein the body includes two or more frames, wherein each frame of the two or more frames includes at least one opening of the plurality of openings.

(11) The device of (10), wherein each frame of the two or more frames includes a respective plurality of structures, wherein the plurality of structures of each frame form a respective plurality of openings in the frame, and wherein the pluralities of structures of the two or more frames form the one or more air spaces.

(12) The device of (11), wherein the plurality of structures is an open-cell structure.

(13) The device of (11), wherein the plurality of structures is a closed-cell structure.

(14) The device of (10), further comprising: one or more hinges, wherein each hinge of the one or more hinges joins two respective frames of the plurality of frames such that the plurality of frames can be changed from an unfolded configuration to a folded configuration and from the folded configuration to the unfolded configuration.

(15) The device of (14), wherein each frame of the plurality of frames includes respective protrusions, and wherein the protrusions are configured to create openings between the frames when the plurality of frames are in the folded configuration.

(16) The device of (15), further comprising a plurality of fasteners, wherein each frame of the plurality of frames includes at least part of a fastener of the plurality of fasteners, and wherein the plurality of fasteners are configured to hold the frames in the folded configuration.

(17) A device comprising a body that includes at least six surfaces and that forms one or more air spaces therein, wherein at least four surfaces, of the six surfaces, include one or more respective openings, wherein each surface of the at least four surfaces is parallel to another surface of the at least four surfaces, wherein at least one of the one or more air spaces is disposed between each surface of the at least four surfaces and the another surface that is parallel to the surface, and wherein each of the one or more respective openings of the at least four surfaces is in fluid communication with at least one of the one or more air spaces; and one or more breathable barriers positioned over at least some of the one or more respective openings of the at least four surfaces, wherein the one or more breathable barriers allow air to flow through the at least some of the one or more respective openings of the at least four surfaces into the one or more air spaces.

(18) The device of (17), wherein the one or more air spaces include a network of air spaces that are in fluid communication with each other.

(19) The device of (17), wherein the one or more of waterproof, breathable barriers are constituted by a waterproof, breathable casing that is configured to enclose the body.

(20) The device of (17), wherein the one or more respective openings of a surface of the at least four surfaces are in fluid communication with the one or more respective openings of the other surface that is parallel to the surface.

(21) A system comprising a magnetic-resonance-imaging device that includes a bore; an air supply; a control device that is configured to control the air supply to supply air; and an airflow device that is connected to the air supply. The airflow device is configured to fit inside the bore, and the airflow device includes a body and one or more breathable barriers. The body forms one or more air spaces therein and includes a plurality of openings, and the one or more air spaces are configured to receive supplied air from the air supply. The one or more breathable barriers are positioned over the plurality of openings. And the body and the one or more breathable barriers are configured to allow the supplied air to exit the body, through the one or more air spaces and the plurality of openings, and flow into the bore.

Various example embodiments will be described hereinafter with reference to the accompanying drawings.

FIG. 1 illustrates an example embodiment of a medical-imaging system 10. The medical-imaging system 10 includes at least one magnetic-resonance-imaging (MRI) device 100; one or more image-generation devices 200, each of which is a specially-configured computing device (e.g., a specially-configured desktop computer, a specially-configured laptop computer, a specially-configured server); and a display device 300.

The MRI device 100 is configured to acquire scan data by using magnetic resonance imaging to scan a region (e.g., area, volume, slice) of an object (e.g., a patient) that is resting on a patient support 110 inside the bore 101 of the MRI device 100. The one or more image-generation devices 200 obtain scan data from the MRI device 100 and generate one or more images of the region of the object based on the scan data. After the one or more image-generation devices 200 generate the one or more images, the one or more image-generation devices 200 send the one or more images to the display device 300, which displays the one or more images.

Figure 2A:
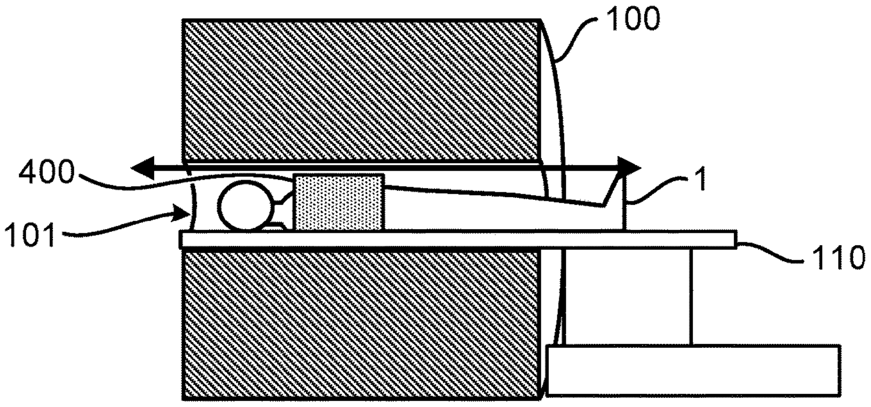
FIG. 2A illustrates a cutaway view of the MRI device along the line A-A in FIG. 1.
Figure 2B:
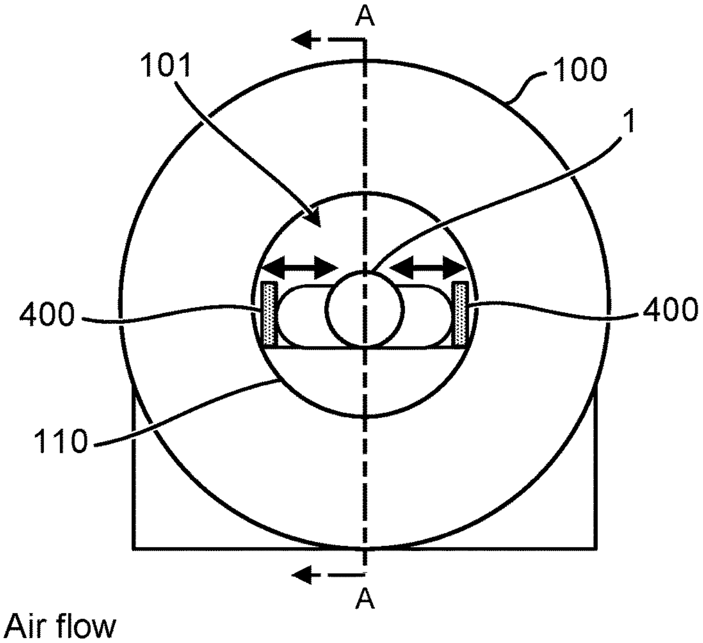
FIG. 2B illustrates a view through the bore of the MRI device.

FIG. 1 shows the MRI device 100 in perspective view. Also, FIG. 2A illustrates a sectional view of the MRI device 100 upon the plane that is indicated by line A-A in FIG. 1, and FIG. 2B illustrates a view through the bore 101 of the MRI device 100. Thus, the view of FIG. 2B is orthogonal to the view of FIG. 2A. A patient 1 is lying on a patient support 110 inside the bore 101 of the MRI device 100 (the patient support 110 and the patient 1 are not shown in sectional view). Also, two airflow devices 400 are located near the shoulders of the patient 1. The airflow devices 400 are patient-positioning devices that allow air to flow through them in multiple directions, which improves the transfer of thermal energy from the patient 1 and helps to protect the patient 1 from thermal-induced injuries.

The radiofrequency (RF) energy in MRI scans can cause RF-induced heating in non-biological objects and biological tissues, and RF-induced heating may cause thermal-induced injuries to biological tissues. Injuries are especially likely where (1) tissue contacts the inner bore liner (the curved surface of the bore 101), where RF near-field burns can occur; (2) tissue contacts tissue in such a way that the body of the patient 1 forms a loop (e.g., linked hands forming a loop through the abdomen and the arms); and (3) tissue contacts cables or other system components capable of inflicting a burn. If there is a sufficiently high likelihood that any of the foregoing contact could occur, then MRI operators are expected to use patient-positioning devices (e.g., padding) to eliminate the contact, thereby reducing or eliminating the chance of serious thermal-induced injury. According to the circumstances, MRI operators may place patient-positioning devices between the patient 1 and the inner bore liner, between the patient 1 and cables or other system components capable of inflicting a burn, or between tissues if contact of the tissues could result in the formation of a loop in the body of the patient 1.

However, the patient-positioning devices obstruct the air flow in the bore 101 of the MRI device 100 (indicated by the dark arrow in FIG. 2A), and the patient-positioning devices also reduce the surface area of a patient's skin that is available to contact the air flow and contribute to the patient's cooling. These cause a reduction in heat transfer from the patient 1 in the confined environment of the bore 101, where the RF energy nearly constantly produces heat during MRI scans.

This reduction in heat transfer from the patient 1 can endanger the patient's well-being in several ways. First, the reduction may create an environment whose local conditions differ from those assumed by standard safety algorithms, such as those for Specific Absorption Rate (SAR), which predicts the heating in biological tissue over time. Second, the obstruction in the bore 101 blocks the flow of forced air for cooling, even when the MRI device's bore fans are enabled, which may increase patient discomfort. And in the claustrophobic environment of the bore 101, discomfort is a significant factor in patient non-compliance and exam cancellation. Third, increased patient complaints and discomfort lead to abandonment of prescribed safety practices by operators who are trying to obtain the full 30-60 minutes of examination. And abandonment of safety practices increases the risk of thermal-induced injuries to the patient 1.

Figure 2C:
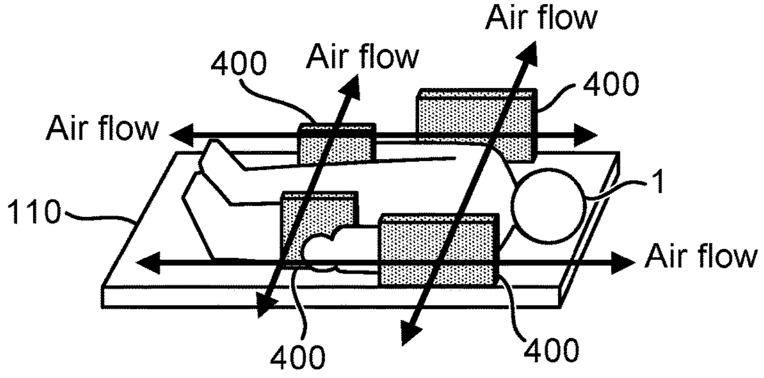
FIG. 2C illustrates example embodiments of airflow devices.

Consequently, each airflow device 400 includes openings and spaces that allow air to flow through the airflow device 400 in at least two directions. For example, FIG. 2C illustrates example embodiments of airflow devices 400, and at least two of the directions in which air can flow through the airflow devices 400 are shown by the dark arrows. The two directions are orthogonal to each other. One direction is parallel to the longitudinal axis of the bore 101, which allows the airflow through the bore 101 to flow through the airflow devices 400. The other direction is perpendicular to the surface of the patient's skin, which allows air to flow to and away from the skin. Examples of the spaces that allow air to flow through them (which may be referred to below as air spaces) include cavities, chambers, tunnels, and conduits.

The airflow through the bore 101 and the airflow to and from the skin increase a patient's ability to dissipate the heat that is generated by the RF energy (e.g., by increasing the skin area that can transfer thermal energy through convective heat transfer), and an increased ability to dissipate the heat decreases the chance of a thermal-induced injury. Furthermore, such airflow increases a patient's comfort, which tends to increase patient compliance and improve MRI image quality.

Additionally, the airflow devices 400 are configured to be easily disinfected and cleaned. Increasing the permeability of a material tends to increase the difficultly of disinfecting and cleaning the material (e.g., because the surface area to be cleaned increases, because some of the surface area to be cleaned is located inside the material and more difficult to access). However, the airflow devices 400 can be easily disinfected and cleaned, and the airflow devices 400 allow air to flow through the airflow devices 400 in multiple directions.

Additionally, the airflow devices 400 are composed of materials that (1) do not have a proton signal and (2) do not have conductive, capacitive, or ferro-magnetic qualities. Also, at least some of the materials may be able to be disinfected in accordance with established infection-control procedures. And, in some embodiments, the materials do not include latex or other materials that commonly trigger allergic reactions in humans.

Moreover, the dimensions of the airflow devices 400 can vary according to the expected conditions of use. Examples of dimensions include the following: 2-4 cm thickness, 10 cm height, and 20 cm length; 2-5 cm thickness, 15 cm height, and 50 cm length; 2-5 cm thickness, 10 cm height, and 25 cm length; 4-8 cm thickness, 10-30 cm height, and 30-60 cm length; and 2-10 cm thickness, 5-25 cm height, and 40-80 cm length. These are just examples, and some embodiments have other dimensions.

Also, the materials that compose the members of the airflow devices 400 may allow the airflow devices 400 to easily permit some compression while resisting compression past a certain point. For example, some embodiments of airflow devices 400 compress to a thickness of no less than 2 cm, and thus have a minimum thickness of 2 cm. This minimum thickness may improve patient safety by maintaining a minimum distance between the patient 1 and the surface of the bore 101. Also, the materials that compose the members of the airflow devices 400 may give the airflow devices 400 some flexibility. For example, some embodiments of airflow devices 400 are flexible enough to conform to the curved surface of the bore 101. However, some embodiments of airflow devices 400 are more rigid.

Accordingly, the resistance to compression and the flexibility of different embodiments of airflow devices 400 may vary depending on their expected conditions of use, and the materials that constitute the airflow devices 400 may be selected accordingly.

Furthermore, the airflow through the airflow devices 400 and, in some embodiments, the waterproof materials that constitute parts of the airflow devices 400, prevent the airflow devices 400 from becoming fully saturated with water-if an airflow device 400 became fully saturated with water, it would also become conductive.

Figure 3A:
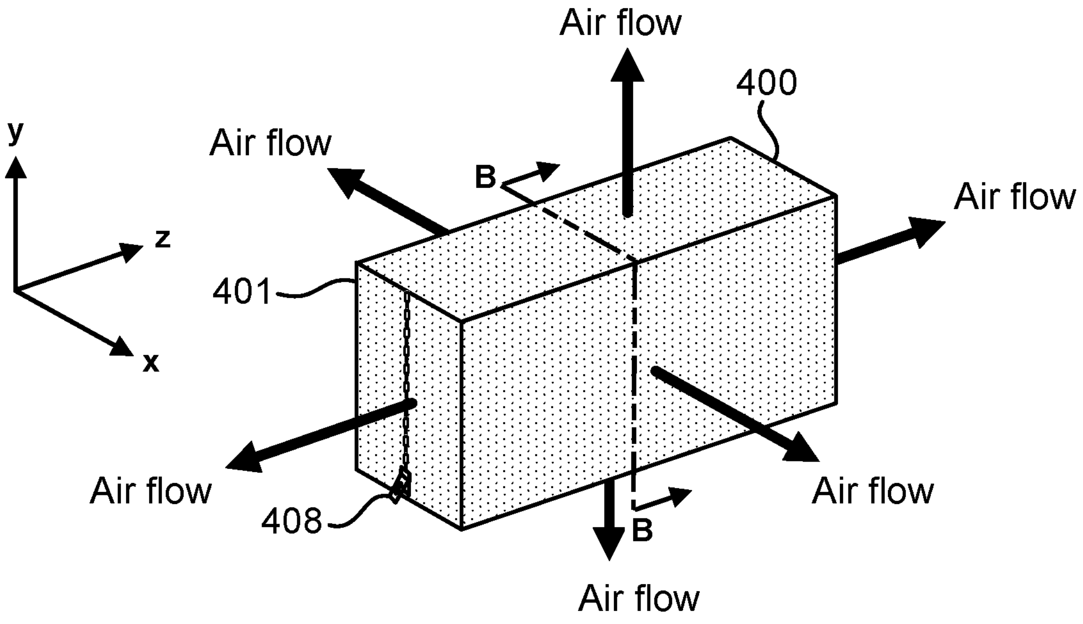
FIGS. 3A and 3B illustrate an example embodiment of an airflow device.
Figure 3B:
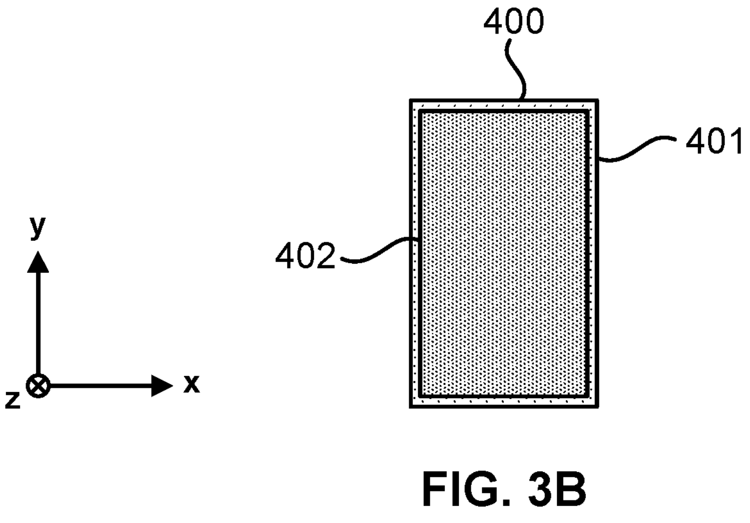

FIGS. 3A and 3B illustrate an example embodiment of an airflow device 400. FIG. 3A illustrates a perspective view of the airflow device 400, and FIG. 3B illustrates a sectional view upon the plane that is indicated by line B-B in FIG. 3A. The airflow device 400 includes one or more breathable barriers and a body 402. The one or more breathable barriers may also be waterproof. The body 402 allows air to flow through it along at least two axes (e.g., the x and z axes). And in this embodiment, the one or more breathable barriers are constituted by a breathable casing 401 (which may also be waterproof) that encloses the body 402.

The casing 401 may be composed of one or more breathable materials, such as breathable fabrics. And the casing 401 may be composed of one or more breathable, waterproof materials, such as breathable, waterproof fabrics. Breathable, waterproof fabrics allow air (including water vapor) to pass through the fabric, but resist the passing of liquid water through the fabric. And breathable, waterproof fabrics prevent the casing 401 from becoming fully saturated with water. Breathable, waterproof fabrics are available in a wide range of breathability and waterproof ratings, and the breathable, waterproof fabric (or fabrics) in the casing 401 can be selected based on the use conditions of the airflow device 400. For example, some breathable, waterproof fabrics have one of the following breathability ratings: 0 to 5,000 $g/m^2$ per day; 5,000 to 10,000 $g/m^2$ per day; 10,000 to 15,000 $g/m^2$ per day; 15,000 to 20,000 $g/m^2$ per day; and more than 20,000 $g/m^2$ per day. Also for example, some breathable, waterproof fabrics have one of the following waterproof ratings: 0 to 5,000 mm; 5,000 to 10,000 mm; 10,000 to 15,000 mm; 15,000 to 20,000 mm; and more than 20,000 mm.

Furthermore, the casing 401 includes a zipper 408, although other embodiments include other fasteners (e.g., buttons, clasps, hook-and-loop fasteners, straps, hook-and-eye closures). The zipper 408 can be used to open and close the casing 401 (e.g., during insertion or removal of the body 402). The zipper 408 (or other fasteners) are composed of materials suitable for use in MRI systems. Also, some embodiments of the casing 401 include draw strings or other closing mechanisms (e.g., a folding closure or flap).

In this embodiment, the body 402 is composed of one or more open-cell foams (e.g., a reticulated foam). The body 402 may be composed of one contiguous piece of open-cell foam, or the body may include multiple non-contiguous pieces of open-cell foam. Examples of open-cell foams include polyurethane foams (e.g., viscoelastic polyurethane foams). Also for example, some embodiments of open-cell foams have an air flow greater than 0.5 l/s, greater than 1.0 l/s, greater than 1.2 l/s, or greater than 1.5 l/s, in standard conditions. The open-cell foam forms many openings on the surfaces of the body 402 and forms many interconnected air spaces. The openings allow air to flow through the surfaces of the body 402 into the air spaces, through the air spaces in multiple directions, and out of the body 402 through other openings.

Thus, air can enter the body 402 through the openings, travel through the body via the air spaces, and exit the body through other openings. Also, air can exit through openings that are on a surface of the body 402 that is different from the surface of the opening through which the air entered, such as a surface that is on the opposite side of the body 402 or a surface that is orthogonal to the surface of the opening through which the air entered. And, in the air spaces, air can mix with air that entered the body 402 from a different direction. Accordingly, the body 402 and the casing 401 allow air to flow (allow air exchange) in any direction. This allows heat to dissipate from the patient's body and allows cooling airflow to circulate through the bore 101, which keeps the patient 1 cooler and makes the patient 1 more comfortable.

Also, the casing 401 may create a waterproof barrier at the exterior ends of the openings in the body 402. This prevents liquids from traveling through the openings in the body 402 into the air spaces. Furthermore, the casing 401 can be easily disinfected using standard clinical measures.

Accordingly, the airflow device 400 allows air flow in multiple directions and can be easily cleaned or disinfected.

Additionally, the one or more open-cell foams that constitute the body 402 may allow some compression of the body 402 while resisting compression past safety limits. And the one or more open-cell foams that constitute the body 402 may provide the body 402 with some ability to conform to the patient 1 or to the curved surface of the bore 101.

Figure 4A:
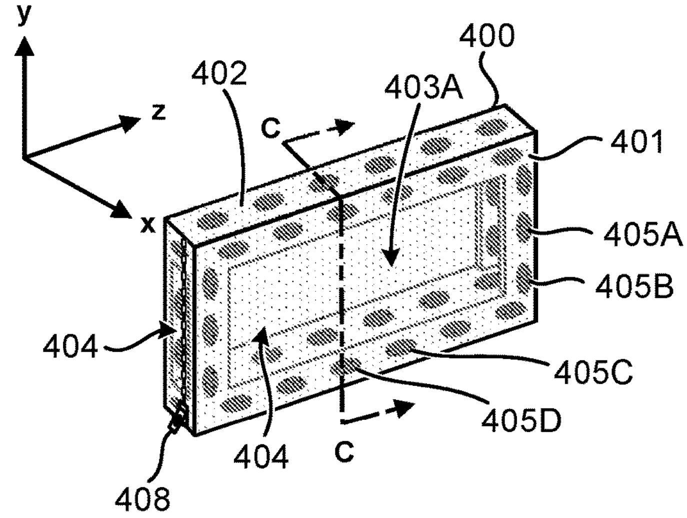
FIGS. 4A-C illustrate an example embodiment of an airflow device.
Figure 4B:
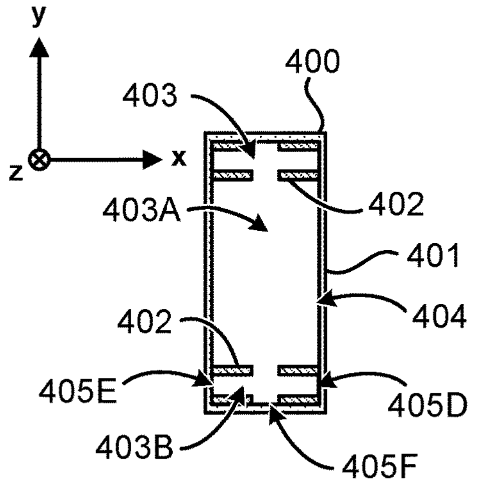
Figure 4C:
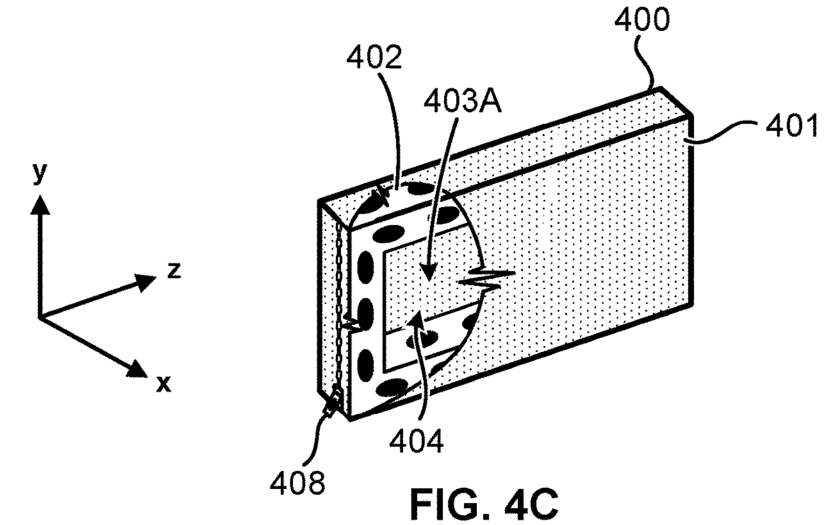

FIGS. 4A-C illustrate an example embodiment of an airflow device 400. FIGS. 4A and 4C illustrate a perspective view of the airflow device 400, and FIG. 4B illustrates a sectional view upon the plane that is indicated by the line CC in FIG. 4A.

The airflow device 400 includes a body 402 and one or more breathable barriers. In this embodiment, the one or more breathable barriers are constituted by a casing 401 that encloses the body 402. The casing 401 is composed of one or more breathable materials, which may also be waterproof. In FIG. 4A, to make the body 402 visible, the casing 401 is illustrated as being partially transparent. In FIG. 4C, the casing 401 is not illustrated as being transparent, but FIG. 4C illustrates a cutaway view through the casing 401.

The body 402 is inflatable and, when inflated, forms a frame that defines multiple air spaces 403 (FIGS. 4A-C show an inflated body 402). Examples of the materials that may compose the body 402 include rubber and plastic (e.g., polyvinyl).

When inflated, the body 402 has central openings 404 in its two largest surfaces. Also, in this embodiment, the body 402 has central openings 404 in two of its smaller surfaces. And, when the body 402 is inflated, a central air space 403A is in direct fluid communication with the central openings 404.

Furthermore, this embodiment of the body 402 includes peripheral openings 405, some of which are in direct fluid communication with smaller air spaces 403. The peripheral openings 405 and smaller air spaces 403 reduce the volume of air needed to inflate the body 402 and improve airflow. In this embodiment, some of the peripheral openings 405, such as peripheral openings 405A-B, are in direct fluid communication with the central air space 403A. However, some of the peripheral openings 405 in FIGS. 4A-C, such as peripheral openings 405C-D, are in direct fluid communication with smaller air spaces 403 that are in fluid communication with the central air space 403A. For example, in this embodiment, a peripheral opening 405D is in direct fluid communication with a smaller air space 403B, which is also in fluid communication with a peripheral opening 405E on the opposite surface of the body 402 and a peripheral opening 405F on the bottom surface of the body 402. But, in some embodiments, all of the peripheral openings 405 are in direct fluid communication with the central air space 403A. And, in some embodiments (e.g., embodiments in which all of the peripheral openings 405 are in direct or indirect fluid communication with the central air space 403A), some of the peripheral openings 405 also allow air to flow through the body 402 along the y axis. Furthermore, in some embodiments, the body 402 includes multiple air spaces 403 that are not in fluid communication with each other, and only a respective proper subset of the openings 404, 405 is in direct or indirect fluid communication with a particular air space 403.

The openings 404 may also allow the body 402 to be more easily cleaned. For example, a user can remove the casing 401, wipe the outer surfaces of the body 402, and reach through the openings 404 to wipe the inner surfaces of the body 402 that line the central air space 403A.

Furthermore, when the casing 401 encloses the body 402, the casing 401 creates a barrier that prevents the traversal of tissue through the openings 404 into the central air space 403A.

Thus, air can enter the body 402 through the openings 404, 405; travel through the body via the air spaces 403; and exit the body 402 through other openings 404, 405. Also, air can exit through openings 404, 405 that are on a surface of the body 402 that is different from the surface of the opening 404, 405 through which the air entered, such as a surface that is on the opposite side of the body 402 or a surface that is orthogonal to the surface of the opening 404, 405 through which the air entered. And, in the air spaces 403, air can mix with air that entered the body 402 from a different direction. For example, air can enter the central air space 403A from any of the six central openings 404 and can exit the central air space 403A by flowing through any of the six central openings 404. Also for example, air can enter the smaller air space 403B through a first peripheral opening 405D and exit the smaller air space 403B by flowing through a second peripheral opening 405E. Accordingly, the body 402 and the casing 401 allow air to flow (allow air exchange) in any direction.

Also, the materials that constitute the body 402 are flexible, which allows the body 402 to change its shape as it is inflated or deflated. The body 402 may also be inflated to an air pressure that provides a desired ability to conform to an object (e.g., the bore 101, the patient 1) or that maintains a minimum thickness.

Furthermore, in embodiments in which the casing 401 is composed of waterproof, breathable materials, the casing 401 creates a waterproof barrier at the exterior ends of the openings 404, 405 (the ends of the openings 404, 405 that are at a surface of the body 402). This prevents liquids from entering the openings 404, 405 and traveling through the air spaces 403. Also, this may help to prevent contaminants (e.g., microorganisms) from entering the openings 404, 405 and traveling through the air spaces 403, which may reduce or eliminate any need to disinfect the openings 404, 405 and the air spaces 403.

Figure 4D:
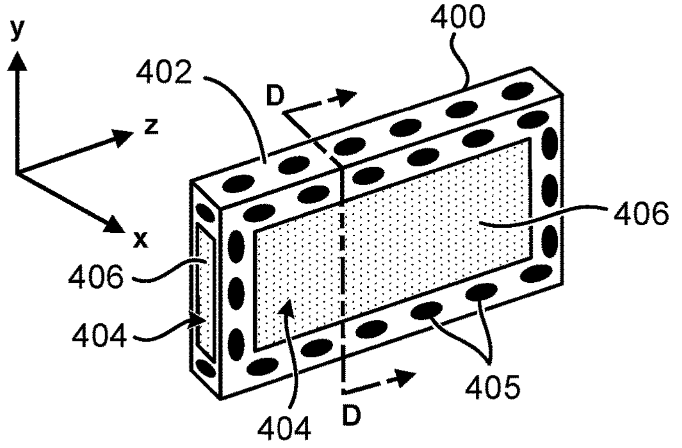
FIGS. 4D-E illustrate an example embodiment of an airflow device.
Figure 4E:
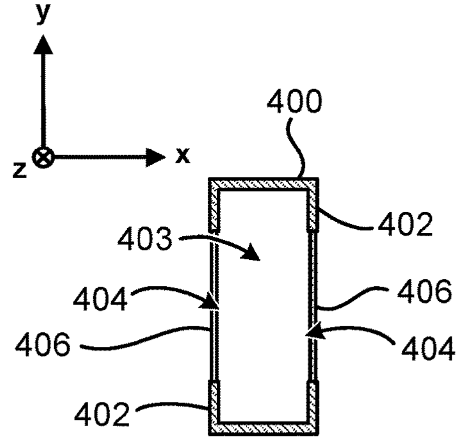

FIGS. 4D-E illustrate an example embodiment of an airflow device 400. FIG. 4D illustrates a perspective view of the airflow device 400, and FIG. 4E illustrates a sectional view upon the plane that is indicated by the line DD in FIG. 4D. Like the embodiment in FIGS. 4A-C, the airflow device 400 includes an inflatable body 402. But, in this embodiment, all of the openings 404, 405 are in direct fluid communication with a single air space 403. Also, the one or more breathable barriers are constituted by panels 406 that are positioned over the central openings 404.

The panels 406 are composed of one or more breathable materials, such as the materials that compose the casing 401 in FIGS. 4A-C. Additionally, the outer surfaces of the panels 406 are located at (flush with, close to) the exterior ends of the openings 404. Also, the panels 406 may be waterproof, and consequently the panels 406 may create waterproof barriers at the exterior ends of the openings 404. This prevents liquids from entering the openings 404 and traveling through the air space 403. Also, this may help to prevent contaminants (e.g., microorganisms) from entering the openings 404 and traveling through the air space 403.

The panels 406 in the embodiments that are described herein may be attached by adhesives or fasteners. Also, the adhesives or fasteners may allow the panels 406 to be easily detached from or attached to the body 402. Examples of fasteners include buttons, hook-and-loop fasteners, clips, clasps, zippers, and sliders. A user may remove the panels 406 to clean or disinfect the surfaces of the body 402 that abut the air space 403.

Moreover, the peripheral openings 405 may be covered by respective panels.

Figure 5A:
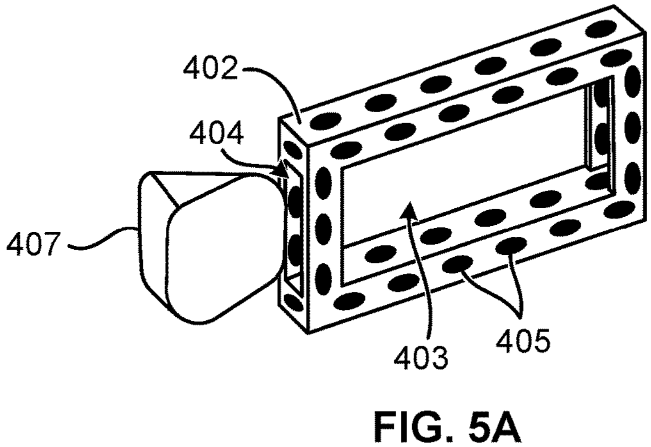
FIG. 5A illustrates an example embodiment of an inflatable body.

FIG. 5A illustrates an example embodiment of an inflatable body 402. The inflatable body 402 includes an air reservoir 407 (e.g., an air bladder), which may help a user to inflate the inflatable body 402. The air reservoir 407 can store air that can be transferred to the inflatable body 402 by compressing the air reservoir 407. Also, the volume of the air reservoir 407 may approximately equal the volume of air that is required to fully inflate the inflatable body 402. And the connection between the air reservoir 407 and the inflatable body 402 may include a valve or a sealing mechanism (e.g., interlocking plastic strips, such as interlocking sliding channels or a sliding zipper lock) that can be used to allow or prevent the flow of air between the air reservoir 407 and the inflatable body 402. Furthermore, the air reservoir 407 and the inflatable body 402 may be a closed system: in some embodiments, air can flow between the air reservoir 407 and the inflatable body 402, but air cannot escape from the collective of the air reservoir 407 and the inflatable body 402, and outside air cannot enter the collective of the air reservoir 407 and the inflatable body 402.

Figure 5B:
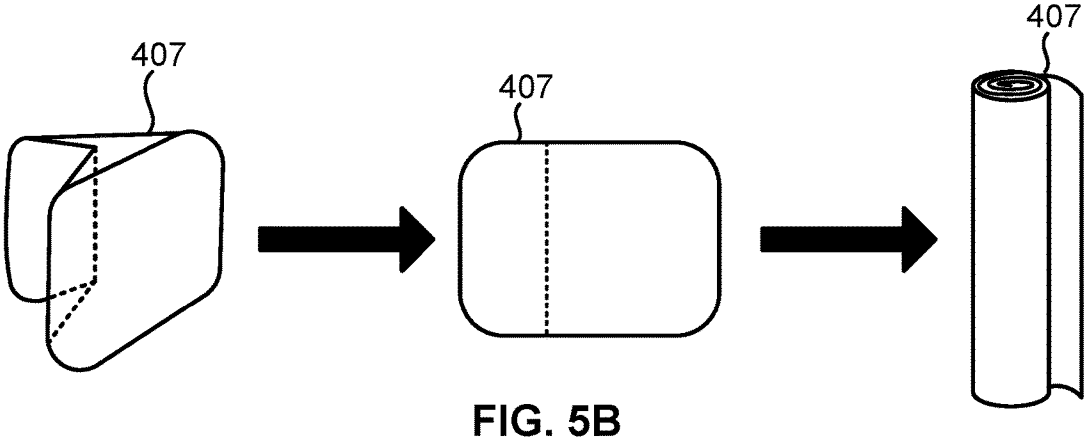
FIG. 5B illustrates an example embodiment of an air reservoir as the air reservoir transitions from partially deflated to fully (or almost fully) deflated and substantially flat, and then from fully (or almost fully) deflated and substantially flat to rolled up.

Once the air has been transferred to the inflatable body 402, the mostly or entirely deflated air reservoir 407 may be flattened and rolled up. For example, FIG. 5B illustrates an example embodiment of an air reservoir 407 as the air reservoir 407 transitions from partially deflated to fully (or almost fully) deflated and substantially flat, and then from fully (or almost fully) deflated and substantially flat to rolled up.

Figure 5C:
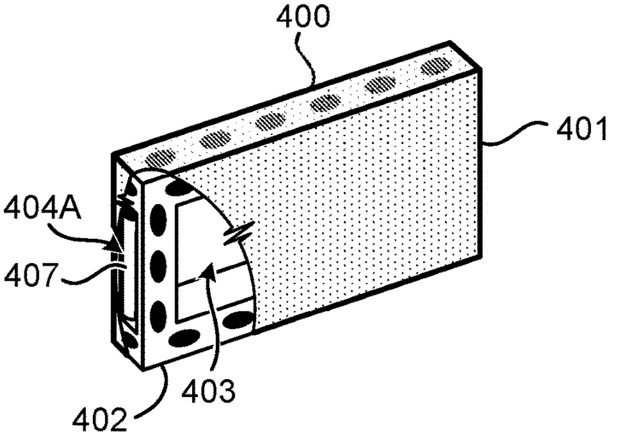
FIG. 5C illustrates an example embodiment of an airflow device.

As illustrated in FIG. 5C, a rolled-up air reservoir 407 can then be inserted into the air space 403 through an opening 404A. The closed casing 401 may then hold the air reservoir 407 in place. Also, if the rolled-up air reservoir 407 is slightly wider than the opening 404A or the air space 403, such that the rolled-up air reservoir 407 has to be deformed to be inserted through the opening 404A into the air space 403, then the outward pressure of the air reservoir 407 may hold the air reservoir 407 in place.

Also, some embodiments include an air pump in addition to, or in alternative to, the air reservoir 407.

Figure 5D:
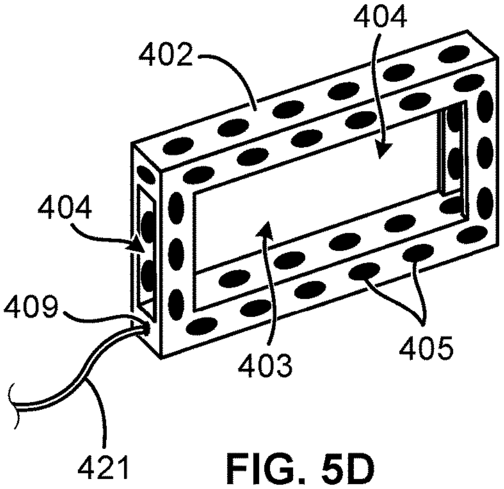
FIG. 5D illustrates an example embodiment of an inflatable body.

FIG. 5D illustrates an example embodiment of an inflatable body 402. In this embodiment, the inflatable body 402 includes a port 409 through which air can be injected by a hose 421 (e.g., a disposable hose) or other conduit that is supplied with air from an external air supply (e.g., a pump, a fan, a compressor). In some embodiments, the port 409 is in fluid communication with the central openings 404 or with one or more of the peripheral openings 405, and the injected air can exit the inflatable body 402 through the openings 404, 405. Also, in some embodiments, the inflatable body 402 is composed of one or more permeable or porous materials, and the injected air can exit the inflatable body 402 by passing through these materials. Moreover, the casing 401 may be configured with an opening for the port 409. Consequently, the inflatable body 402 can allow additional airflow to be delivered to a patient's skin, which may provide additional cooling. And other embodiments of the body 402 that are described herein may also include a port 409 through which air can be injected by an external air supply.

Figure 6A:
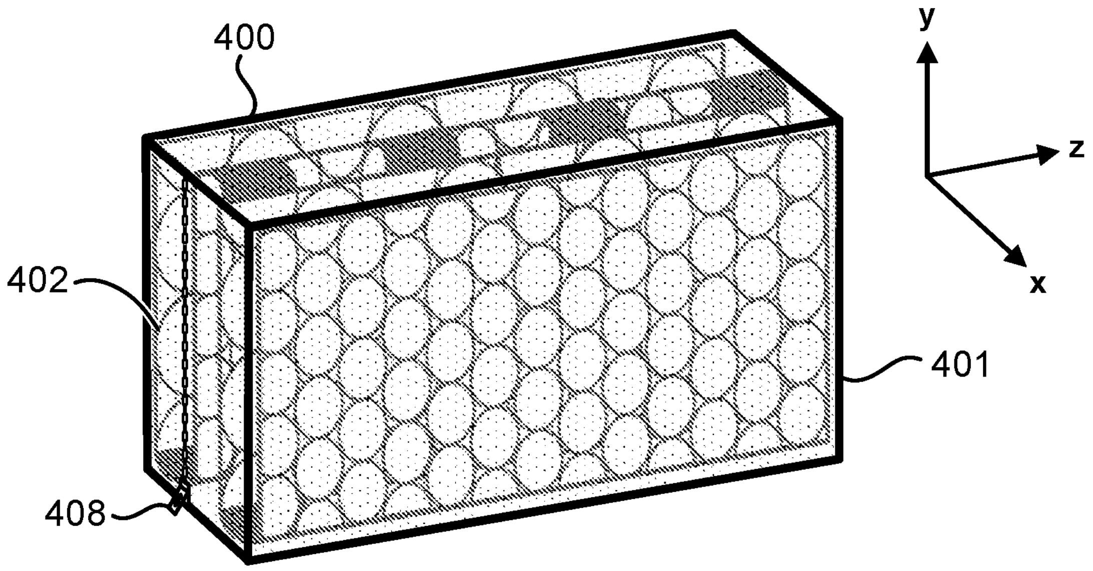
FIGS. 6A-B illustrate an example embodiment of an airflow device.
Figure 6B:
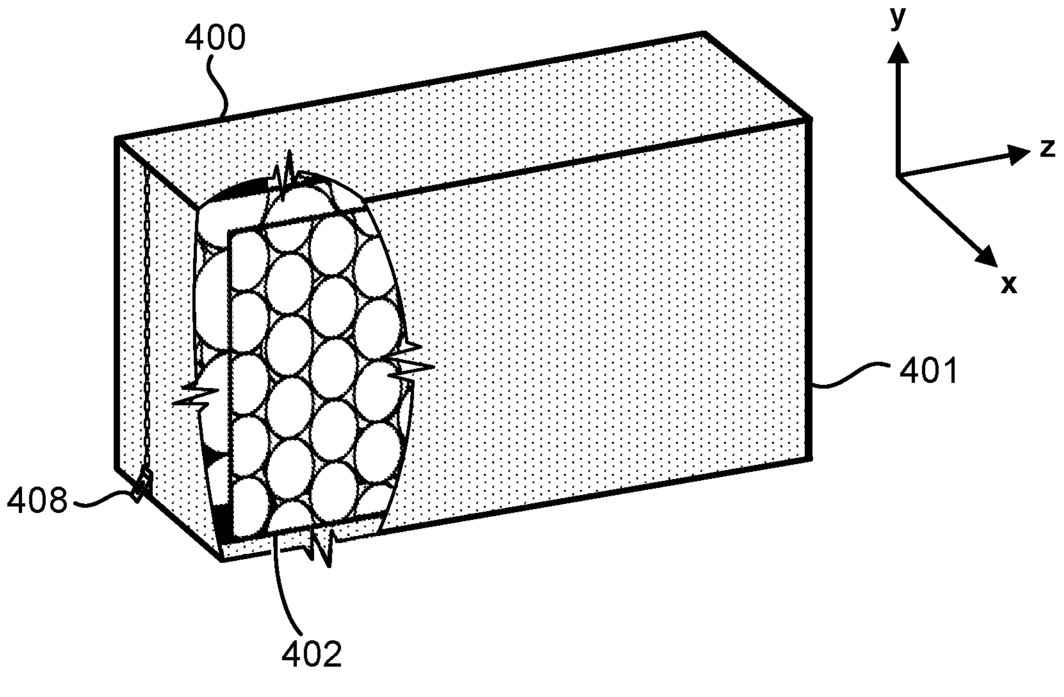

FIGS. 6A-B illustrate an example embodiment of an airflow device. The airflow device 400 includes a foldable body 402 and one or more breathable barriers. In this embodiment, the one or more breathable barriers are constituted by a breathable casing 401 that encloses the body 402. Also, the casing 401 includes a zipper 408 (or other fastening device or closing mechanism), and the casing 401 may be waterproof. In FIG. 6A, to make the foldable body 402 visible, the casing 401 is illustrated as being partially transparent. In FIG. 6B, the casing 401 is not illustrated as being transparent, but FIG. 6B illustrates a cutaway view through the casing 401.

Figure 7A:
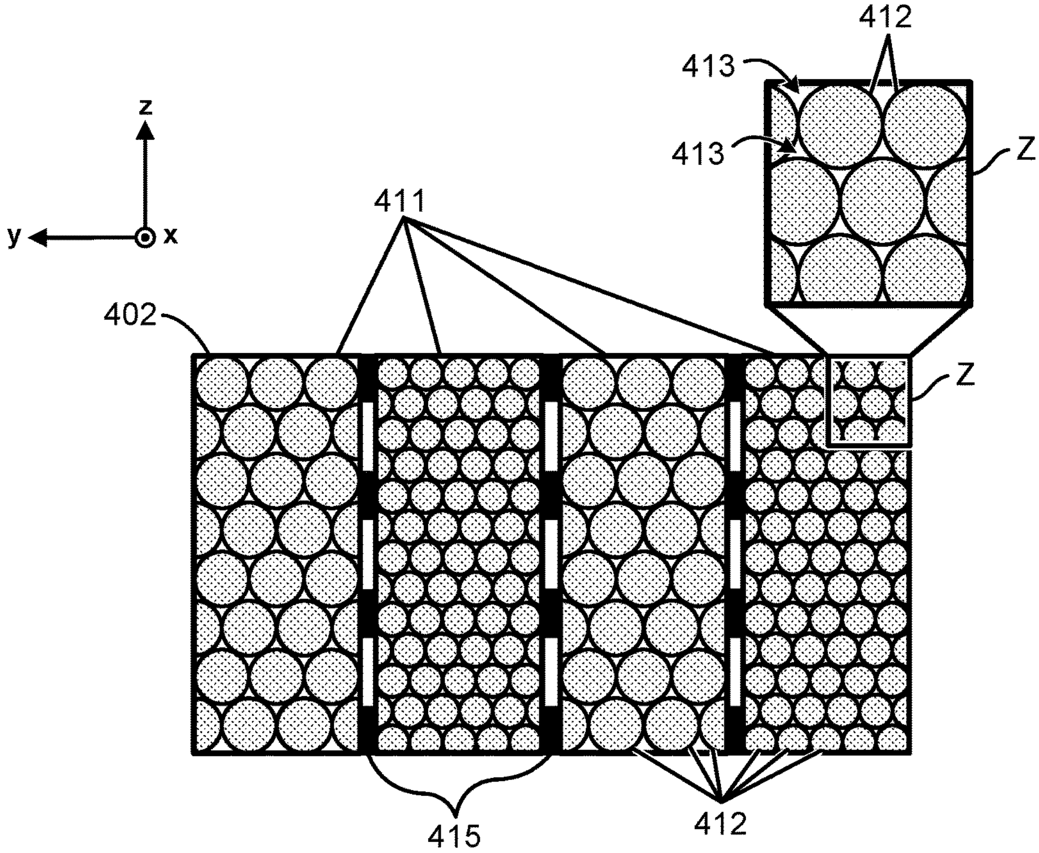
FIGS. 7A-C illustrate an example embodiment of a foldable body.
Figure 7B:
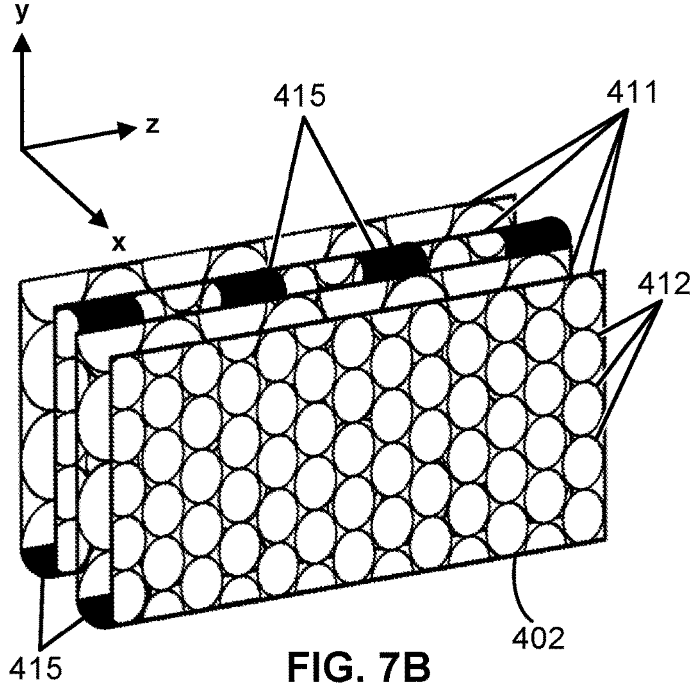
Figure 7C:
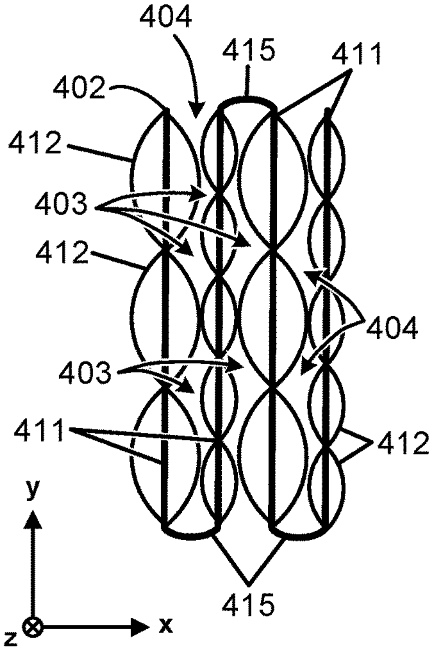

And FIGS. 7A-C illustrate an example embodiment of the foldable body 402 from FIGS. 6A-B. FIG. 7A illustrates the foldable body 402 in the unfolded configuration. FIG. 7B illustrates a perspective view of the foldable body 402 in the folded configuration. And FIG. 7C illustrates a side view of the foldable body 402 in the folded configuration.

The foldable body 402 includes a plurality of frames 411 (four frames 411 in this example embodiment). Each of the frames 411 includes a plurality of respective structures 412. Also, there are openings 413 between the structures 412 of a frame 411. The openings 413 in a frame 411 allow air to flow though the frame 411 (to flow through the frame 411 along the x axis in FIGS. 6A, 6B, 7A, 7B, and 7C). For example, the insert in FIG. 7A shows a magnified view of region Z of one of the frames 411, and region Z includes structures 412 and openings 413.

The frames 411 in this embodiment are joined by hinges 415, which allow the frames 411 to be folded and unfolded. Examples of hinges 415 includes flag hinges, snap hinges, finger hinges, and barrel hinges, although some embodiments use other types of hinges. Also, in some embodiments, the hinges 415 are formed by hook-and-loop fasteners. The hinges 415 may be configured for easy connection and separation, which may allow the frames 411 to be easily connected or disconnected from each other. This in turn may allow a user to adjust the thickness of the body 402 by adding or removing frames 411. Also, the hinges 415 may allow the frames 411 to be folded into different configurations, and various configurations may exchange thickness for surface area or vice versa. For example, four frames 411 may be folded into a folded configuration that has a length (z-axis dimension) of one frame, a height (y-axis dimension) of two frames 411, and a thickness (x-axis dimension) of two frames 411

Furthermore, the frames 411 may include fasteners (e.g., snaps, hook-and-loop fasteners) that can secure the frames 411 in the folded configuration. For example, the surface of a first frame 411 that faces a surface of a second frame 411 may include a male snap or a hook patch, and the surface of the second frame 411 may include a female snap or a loop patch that is positioned to contact the male snap or hook patch when the first and second frames 411 are folded together.

In some embodiments, such as the embodiment in FIGS. 7A-C, the structures 412 are a network of filaments that support a plurality of nodes. Also, the structures 412 are configured to form openings 404 between the frames 411 when the frames 411 are in the folded configuration. For example, in FIGS. 7A-C, the structures 412 of a frame 411 have a configuration (e.g., size, spacing, layout) that is different from the configurations of the structures 412 of the adjacent frames 411. Thus, when the body 402 is in the folded configuration, the structures 412 hold the frames 411 apart from each other, which creates openings 404 between the frames 411.

The structures 412 and the openings 404, 413 form a network of air spaces 403 that are in fluid communication with each other (are interconnected). Thus, air can enter the body 402 through the openings 404, 413; travel through the body via the network of air spaces 403; and exit the body 402 through other openings 404, 413. Also, air can exit through a side or a surface of the body 402 that is different from the side or the surface of the opening 404, 413 through which the air entered, such as an opening 404, 413 in a side or a surface that is on the opposite side of the body 402. And, in the air spaces 403, air can mix with air that entered the body 402 from a different direction.

The structures 412 and the openings 404, 413 create a network of air spaces 403 that are in fluid communication with each other and that allow air to flow through the body 402 in any direction (to flow along the x, y, or z axes in FIGS. 6A-B and 7B-C) when the frames 411 are in the folded configuration.

A user may be able to more easily clean the body 402 by unfolding the frames 411. When the frames 411 are unfolded, more of their surfaces are exposed, and a user can easily wipe or disinfect the frames 411.

And some embodiments of the foldable body 402 omit the hinges 415 and include fasteners to secure the frames 411 together. These embodiments allow a user to selectively attach and detach frames 411, which enables the user to adjust the thickness of the foldable body 402. Furthermore, the frames 411 can be attached in configurations that are different from the configuration in FIG. 7B. For example, four frames 411 may be attached in a configuration that has a length (z-axis dimension) of one frame, a height (y-axis dimension) of two frames 411, and a thickness (x-axis dimension) of two frames 411. And a user can detach the frames 411 from each other to easily access the surfaces of the frames 411 during cleaning or disinfection.

Additionally, the frames 411 may include joinery structures that can secure the frames 411 together, particularly in the folded configuration. Examples of joinery structures include dovetail joints, bridle joints, mortise-and-tendon joints, dowel joints, box joints, groove joints, and tongue-and-groove joints.

The structures 412 may include closed nodes (e.g., closed plastic cells, such as medical-grade foam; closed rubber cells). And the closed nodes can also enclose a filler, such as non-ferrous sand. The extra weight from a filler may allow the body 402 to also be used to immobilize a member (e.g., arm, leg) of a patient.

Figure 8A:
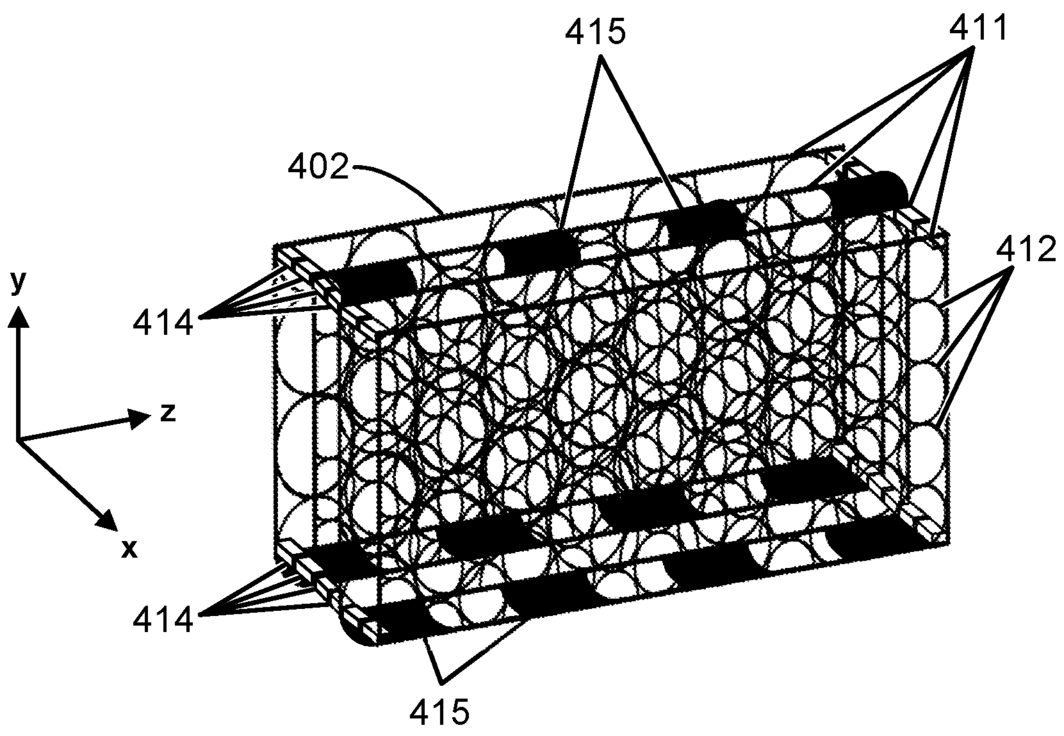
FIGS. 8A and 8B illustrate an example embodiment of a foldable body.
Figure 8B:
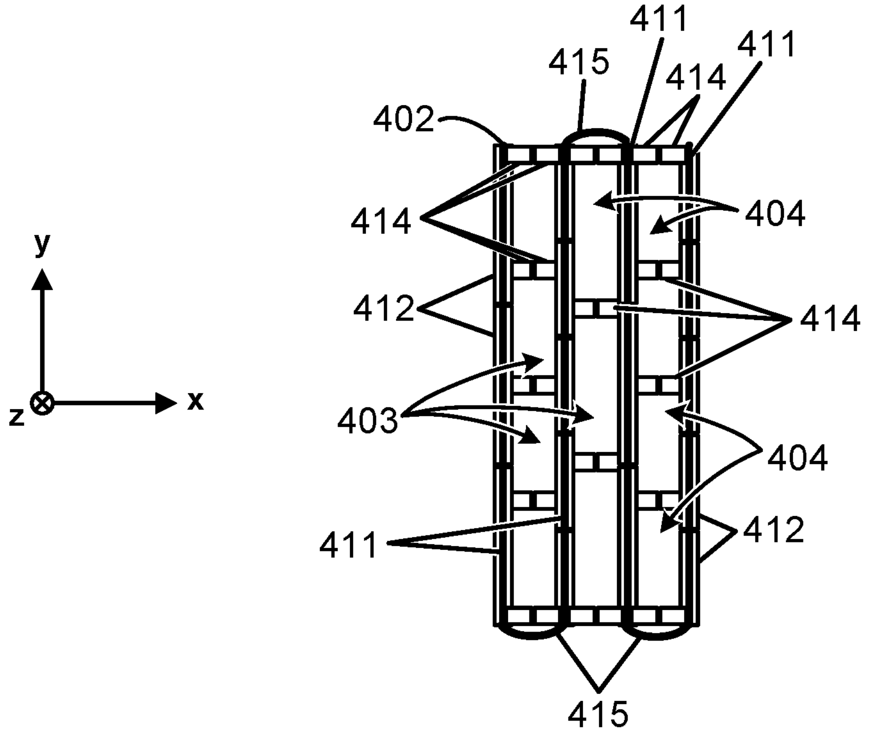

However, the structures 412 may also include open nodes (e.g., open cells). For example, FIGS. 8A and 8B illustrate an example embodiment of a foldable body 402. In this embodiment, the structures 412 are a network of filaments that support open cells. Also, the frames 411 in this embodiment include protrusions 414 (e.g., bosses, flanges, spacers, rims) that are configured to hold the frames 411 away from each other when the frames 411 are in the folded configuration. This forms openings 404 between the frames 411 when the frames 411 are in the folded configuration.

Figure 9A:
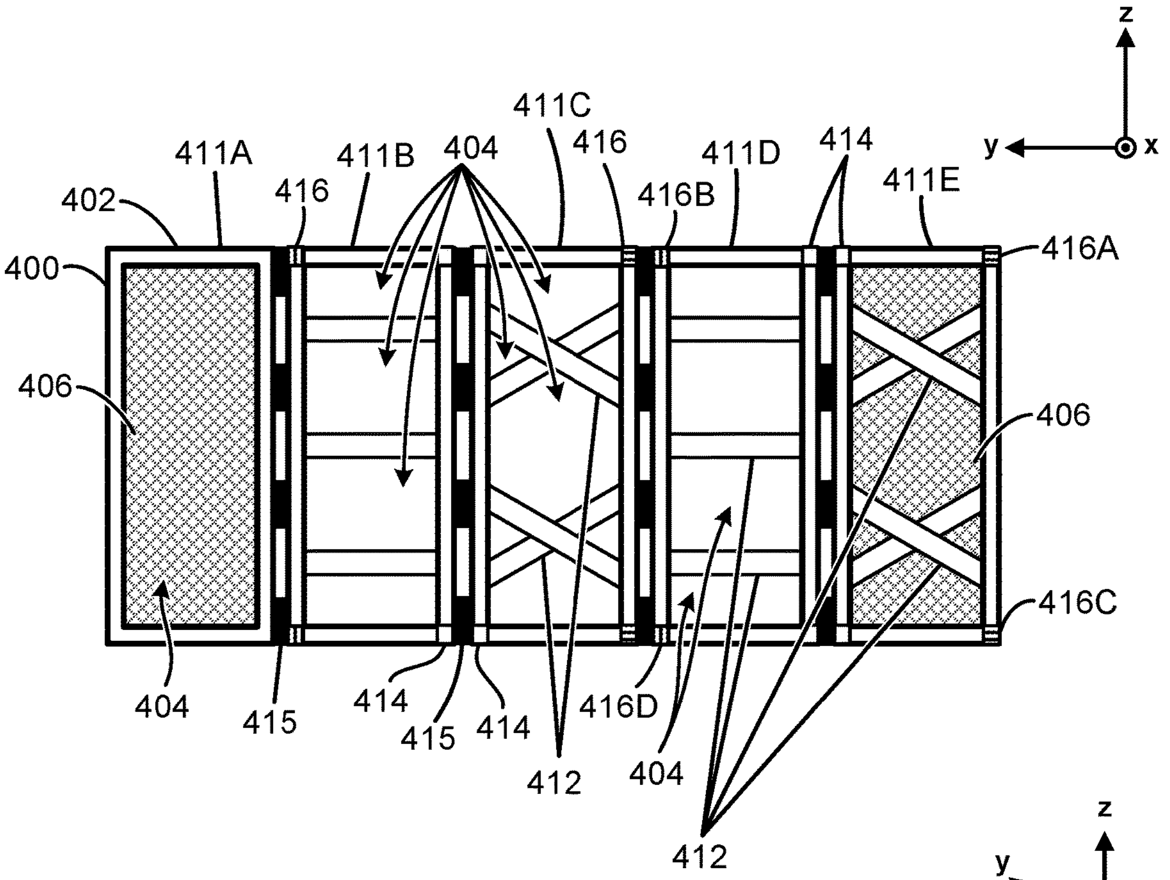
FIG. 9A illustrates an example embodiment of an airflow device.
Figure 9B:
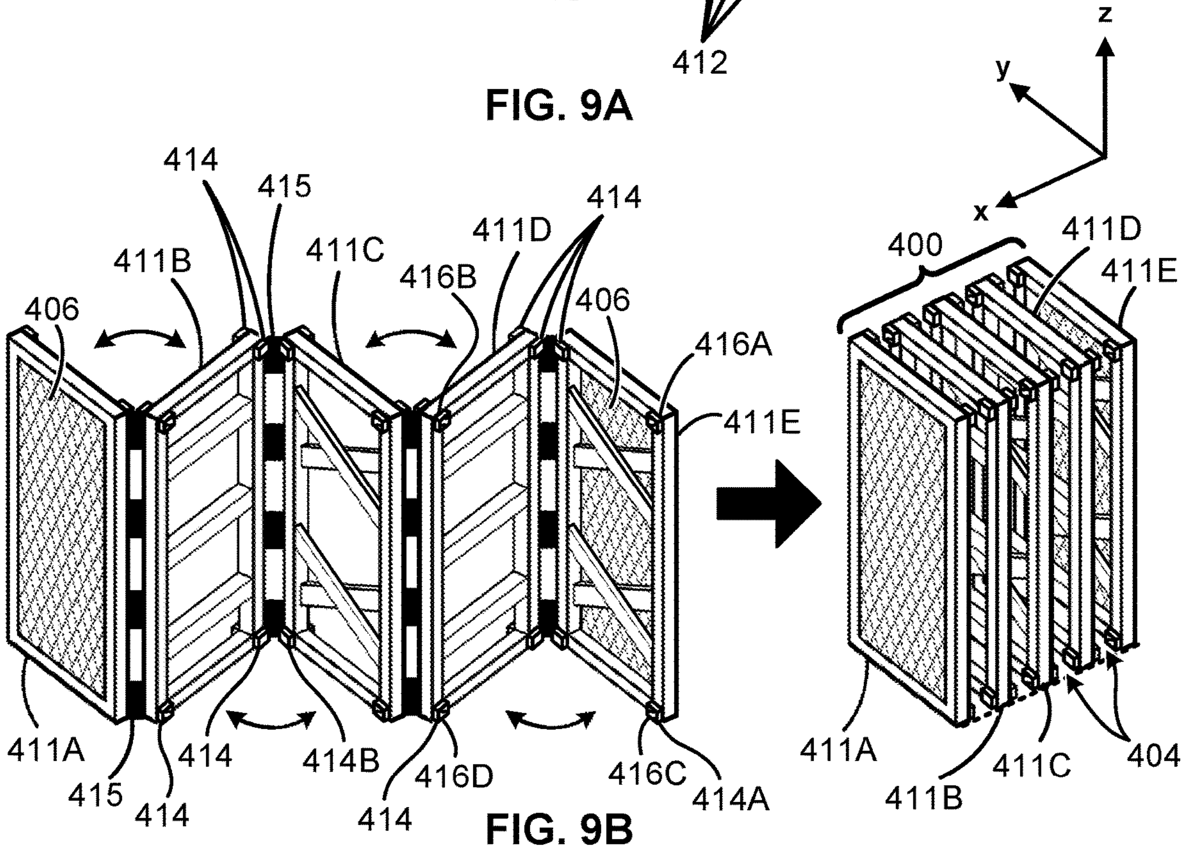
FIG. 9B illustrates the airflow device from FIG. 9A as the airflow device transitions from a partially folded configuration to a completely (or almost completely) folded configuration.

FIG. 9A illustrates an example embodiment of an airflow device 400, and FIG. 9B illustrates the airflow device 400 from FIG. 9A as the airflow device 400 transitions from a partially folded configuration to a completely (or almost completely) folded configuration. Also, the completely (or almost completely) folded airflow device 400 in FIG. 9B is illustrated in an exploded view. As illustrated in FIG. 9B, the frames 411 can be folded in an accordion fold.

The airflow device 400 includes a foldable body 402, which includes five frames 411 in this embodiment, and two or more breathable barriers, which may also be waterproof. All of the frames 411 have respective central openings 404. The frames 411 may be rigid or semi-rigid. The materials that compose the frames 411 may provide the frames 411 with some ability to compress and conform, which may increase patient comfort, while resisting compression past safety limits.

In this embodiment, the two or more breathable barriers are constituted by breathable panels 406 (which may also be waterproof). The frame 411A on the left end and the frame 411E on the right end (the end frames 411A, E) each include a respective panel 406 over their respective central openings 404. The panels 406 allow air to flow through them, and the panels 406 made be composed of the same materials as a casing or a panel from the other embodiments that are described herein. Furthermore, the panels 406 prevent the traversal of tissue through the central openings 404 of the end frames 411A, E.

Also, all of the frames 411 include structures 412. The structures 412 may provide extra structural support for the frames 411 while minimizing any obstruction of the flow of air through the central openings 404. Furthermore, the configurations of the structures 412 may be adjusted to configure the rigidity of the frames 411. When the body 402 is in the folded configuration, the central openings 404 and the structures 412 form a network of air spaces that are in fluid communication with each other. In the embodiment in FIG. 9A, the configurations of the structures 412 vary between adjacent frames 411. This variation may improve the flow of air in multiple directions. However, in some embodiments the configurations of the structures 412 in all the frames 411 are identical.

The structures 412 of the end frames 411A, E are positioned such that their respective structures 412 will be positioned on the interior sides of the panels 406 when the body 402 is in the folded configuration. Thus, in FIG. 9A, the structures 412 on the right end frame 411E are visible, but the structures on the left end frame 411A are not.

Also, the embodiment of the body 402 in FIGS. 9A and 9B includes four joints that have hinges 415 (four hinged joints). Examples of the hinges 415 include stitched hinges, seamed hinges, flag hinges, snap hinges, finger hinges, and barrel hinges, although some embodiments use other types of hinges. Also, each hinged joint has four respective hinges 415 in this embodiment. The gaps between the hinges 415 may form additional openings between the frames 411 when the body 402 is in the folded configuration. And some embodiments of the body 402 include more or fewer hinges 415 per hinged joint. Furthermore, note that the exploded view of the body 402 in FIG. 9B omits the hinges 415.

The hinges 415 may be configured for easy connection and separation. This in turn may allow a user to adjust the thickness of the body 402 or the shape of the folded configuration by adding or removing frames 411. Also, the hinges 415 may allow the frames 411 to be folded into different configurations. And some embodiments of the foldable body 402 omit the hinges 415 and include fasteners or joinery structures that can secure the frames 411 together. Furthermore, the frames 411 can be attached (by hinges 415, by fasteners, or by joinery structures) in configurations that are different from the configuration in FIGS. 9A-B.

The frames 411 also include protrusions 414, which hold the frames 411 apart from each other when the body 402 is in the folded configuration. This separation between the frames 411 forms openings 404 that allow air to flow between the frames 411 when the body 402 is in the folded configuration.

The frames 411 also include fasteners 416 that can hold the frames in the folded configuration. In this embodiment, each fastener 416 is positioned on a respective protrusion 414 (although not all protrusions 414 have fasteners 416 positioned thereon). For example, fastener 416C is positioned on protrusion 414A. However, protrusion 414B does not have a fastener positioned thereon.

The fasteners 416 on frames 411 that contact each other when the body 402 is in the folded configuration (which may be referred to herein as corresponding fasteners 416) are configured to fasten together, thereby holding the body 402 in the folded configuration. For example, the right end frame 411E includes two fasteners 416A and 416C. Also, the adjacent frame 411D includes two fasteners 416B and 416D. When the body 402 is in the folded configuration, fastener 416A contacts fastener 416B, and fastener 416C contacts fastener 416D. And fastener 416A is configured to fasten to fastener 416B, and fastener 416C is configured to fasten to fastener 416D. For example, fastener 416A may be a patch of a hook portion of a hook-and-loop fastener, and fastener 416B may be a patch of a loop portion of a hook-and-look fastener. Also, fastener 416A may be a male snap, and fastener 416B may be a female snap.

When the body 402 is in the folded configuration, each of the three middle frames 4111B-D has two facing (abutting) frames 411, and each of the end frames 411A and 411E has only one facing frame 411. And, as the body 402 is folded, corresponding fasteners 416 are brought into to contact with each other and fastened together. For example, corresponding fasteners 416A-B are brought into contact with each other and fastened together, and corresponding fasteners 416C-D are brought into contact with each other and fastened together. The fasteners 416 that are fastened together hold the body 402 in the folded configuration. And, in the folded configuration, the frames 411 are substantially parallel to each other.

When the frames 411 are in the folded configuration, the frames 411, the structures 412, the protrusions 414, and the openings 404, 405 create an air space (or a network of air spaces that are in fluid communication with each other) and allow air to flow into, flow through, and flow out of the body 402 in any direction (to flow along the x, y, or z axes in FIGS. 9A and 9B). And, in the air space (or network of air spaces), air can mix with air that entered the body 402 from a different direction.

Figure 10A:
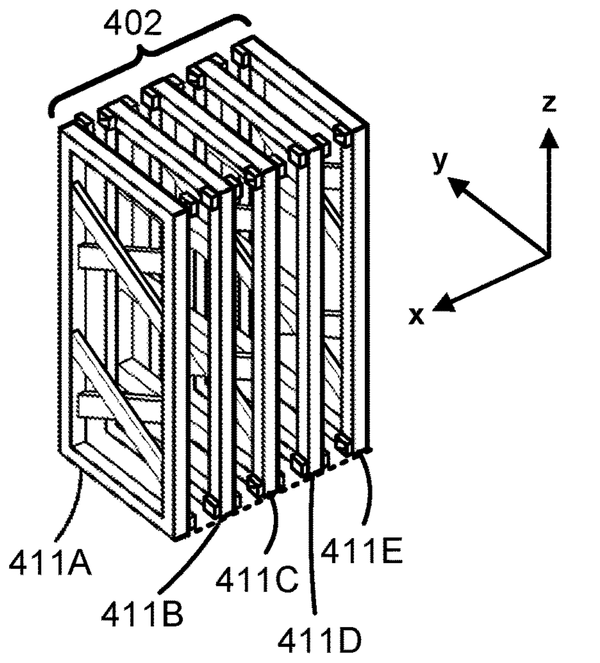
FIG. 10A illustrates an example embodiment of a foldable body.

FIG. 10A illustrates an example embodiment of a foldable body 402. FIG. 10A illustrates an exploded view of the foldable body 402, although FIG. 10A does not illustrate the hinges 415 (which are illustrates in FIGS. 10B-C). The foldable body 402 is the same as the foldable body 402 from FIGS. 9A-B. However, no panels are attached to the foldable body 402.

Figure 10B:
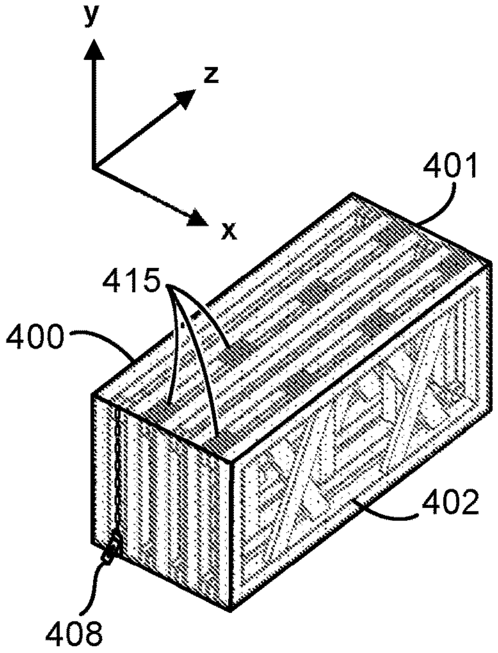
FIGS. 10B-C illustrate an example embodiment of an airflow device that includes the foldable body from FIG. 10A.
Figure 10C:
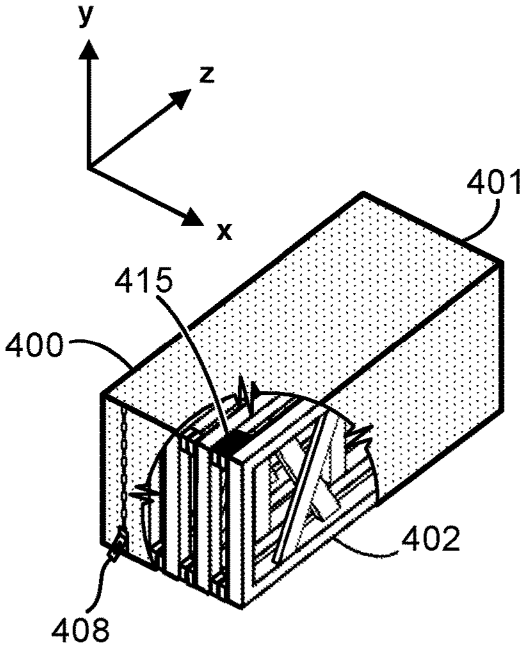

FIGS. 10B-C illustrate an example embodiment of an airflow device 400 that includes the foldable body 402 from FIG. 10A. Both FIGS. 10B-C illustrate a perspective view of the airflow device 400. Also, both FIGS. 10B-C illustrate the hinges 415. In this embodiment, the one or more breathable barriers are constituted by a breathable casing 401, which may also be waterproof. In FIG. 10B, to make the body 402 visible, the casing 401 is illustrated as being partially transparent. In FIG. 10C, the casing 401 is not illustrated as being transparent, but FIG. 10C illustrates a cutaway view through the casing 401.

Figure 11A:
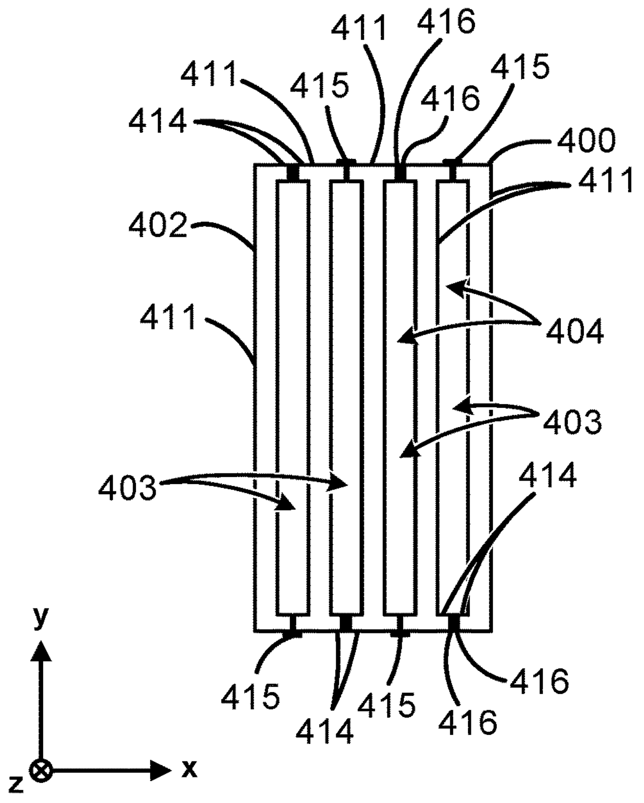
FIG. 11A illustrates a view of an end of the foldable body from FIGS. 9A-B and 10A-C while the body is in the folded configuration.

FIG. 11A illustrates a view of an end surface of the foldable body 402 from FIGS. 9A-C and 10A-C while the body 402 is in the folded configuration. As shown in FIG. 11A, the protrusions 414 hold the frames 411 apart, which forms openings 404 between the frames 411.

Consequently, when the frames 411 in FIGS. 9A-C, 10A-C, and 11A are in the folded configuration, the frames 411, the structures 412, and the openings 404 (*i*) create an air space or a network of air spaces 403 that are in fluid communication with each other and (ii) allow air to flow into, flow through, and flow out of the body 402 in any direction (to flow along the x, y, or z axes in FIGS. 9A-B, 10A-C, and 11A). And, in the network of air spaces 403, air can mix with air that entered the body 402 from a different direction.

Figure 11B:
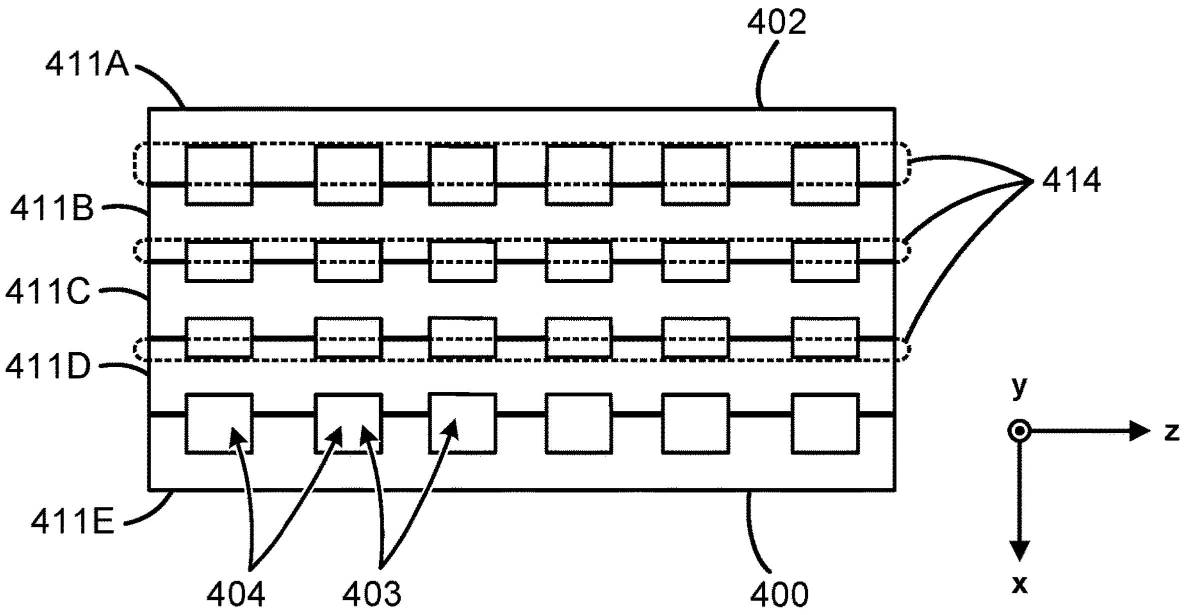
FIG. 11B illustrates a view of the top of an example embodiment of a foldable body.

FIG. 11B illustrates a view of the top of an example embodiment of a foldable body 402. Note that the view in FIG. 11A is parallel to the z axis, and the view in FIG. 11B is parallel to the y axis. Thus, the view in FIG. 11A is orthogonal to the view in FIG. 11B. The foldable body 402 in FIG. 11B is similar to the foldable body 402 in FIGS. 9A-B, 10A-C, and 11A. However, the frames 411 in FIG. 11B include additional protrusions 414 around the perimeters of the frames 411. In this example embodiment, the protrusions 414 give the profiles of the frames 411 an appearance similar to a square wave.

The protrusions 414 create openings 404 on the top, bottom, and ends of the body 402 when the body 402 is in the folded configuration. By holding the frames 411 apart and creating openings 404 on the top, bottom, and ends of the body 402, the protrusions 414 allow air to flow along the y and z axes. Also, the additional protrusions 414 may provide additional structural strength. For example, the additional protrusions 414 may help the frames 411 to resist collapsing when forces are applied to the foldable body 402 along the x axis.

Figure 12A:
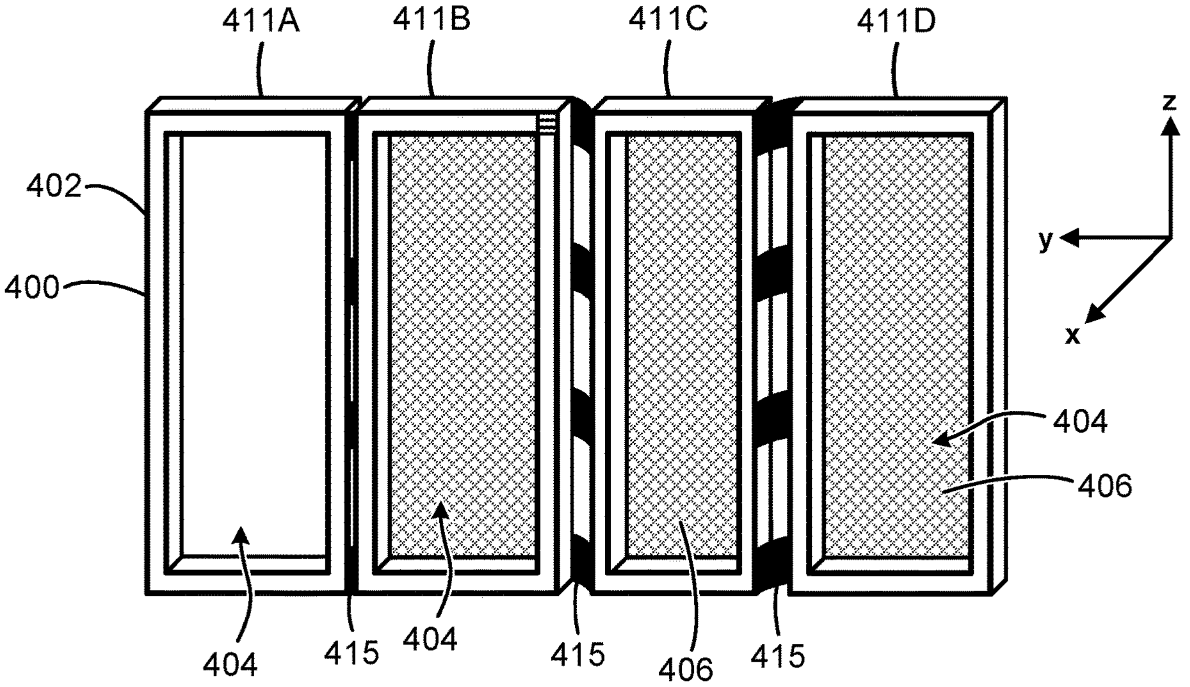
FIGS. 12A-C illustrate an example embodiment of an airflow device.
Figure 12B:
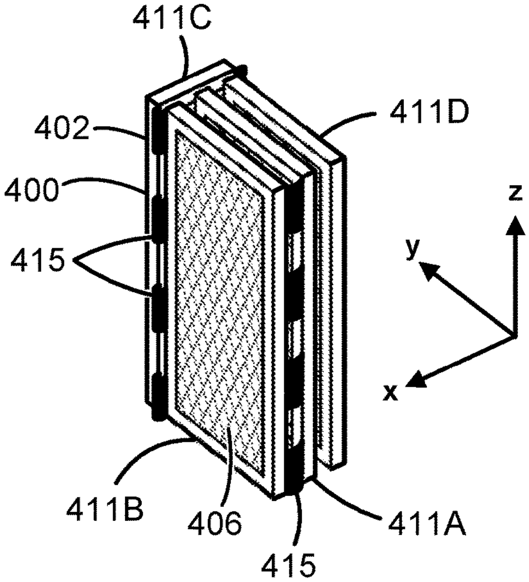
Figure 12C:
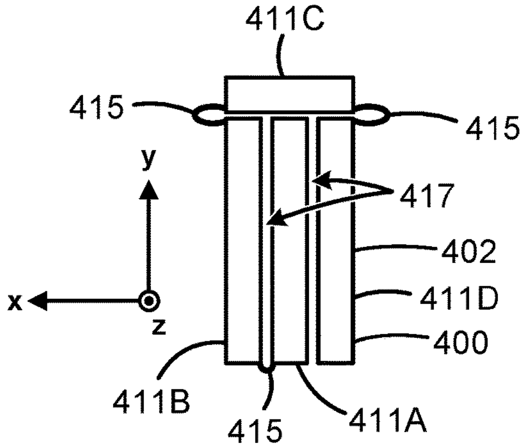

FIGS. 12A-C illustrate an example embodiment of an airflow device. FIG. 12A illustrates a perspective view of the airflow device 400 in the unfolded configuration, and FIG. 12B illustrates a perspective view of the airflow device 400 in the folded configuration. Also, FIG. 12C illustrates a view of an end surface of the airflow device 400 in the folded configuration.

The airflow device 400 includes a foldable body 402, which includes four frames 411 in this embodiment, and three breathable barriers, which may also be waterproof. The frames 411 are similar to the frames 411 in FIGS. 9A-B and 10A-C. However, in this embodiment, the frames 411 do not include any structures, any protrusions, or any fasteners (although in some embodiments at least some of the frames 411 include one or more structures, one or more protrusions, or one or more fasteners). Also, the frames 411 do not have identical widths. For example, the width of the second frame from the right 411C (the narrower frame 411C) has a width that is less than the widths of the other three frames 411A, B, D.

In this embodiment, the three breathable barriers are constituted by breathable panels 406 (which may also be waterproof). The three frames 411B-D on the right include respective panels 406 over their respective central openings 404. The panel 411A on the left does not include a panel. Also, some embodiments have other arrangements of panels 406. For example, in some embodiments, the narrower frame 411C does not include a panel.

Furthermore, the body 402 includes three joints that have hinges 415 (three hinged joints). The gaps 417 between the hinges 415 may form additional openings between the frames 411 when the body 402 is in the folded configuration. And some embodiments of the body 402 include more or fewer hinges 415 per hinged joint.

When the body 402 is in the folded configuration, three of the frames 411A, B, D are parallel or substantially parallel to each other. The narrower frame 411C is orthogonal or substantially orthogonal to the other frames 411A, B, D. Also, when the body 402 is in the folded configuration, there are gaps 417 between the frames 411.

When the frames 411 are in the folded configuration, the frames 411, the openings 404, and the gaps 417 create an air space (or a network of air spaces that are in fluid communication with each other) and allow air to flow into, flow through, and flow out of the body 402 in any direction (to flow along the x, y, or z axes in FIGS. 9A and 9B). And, in the air space (or network of air spaces), air can mix with air that entered the body 402 from a different direction.

Figure 13A:
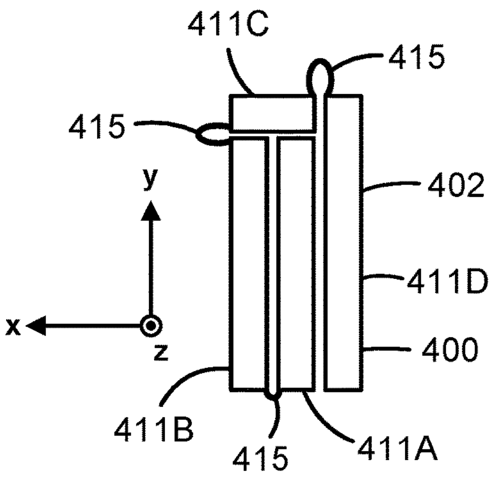
FIG. 13A illustrates a view of an end surface of an example embodiment of an airflow device in the folded configuration.

FIG. 13A illustrates a view of an end surface of an example embodiment of an airflow device 400 in the folded configuration. The frames 411 are similar to the frames in FIGS. 12A-C. However, in this embodiment, the frames 411 have three different widths: One frame 411D is wider than all the others, one frame 411C is narrower than all the others, and two frames 411A-B have widths that are identical to each other. Thus, the airflow device 400 has a different folded configuration than the airflow device 400 in FIGS. 12A-C.

Figure 13B:
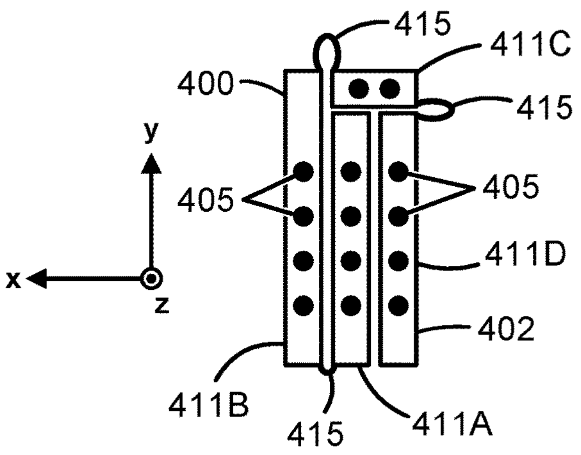
FIG. 13B illustrates a view of an end surface of an example embodiment of an airflow device in the folded configuration.
Figure 15A:
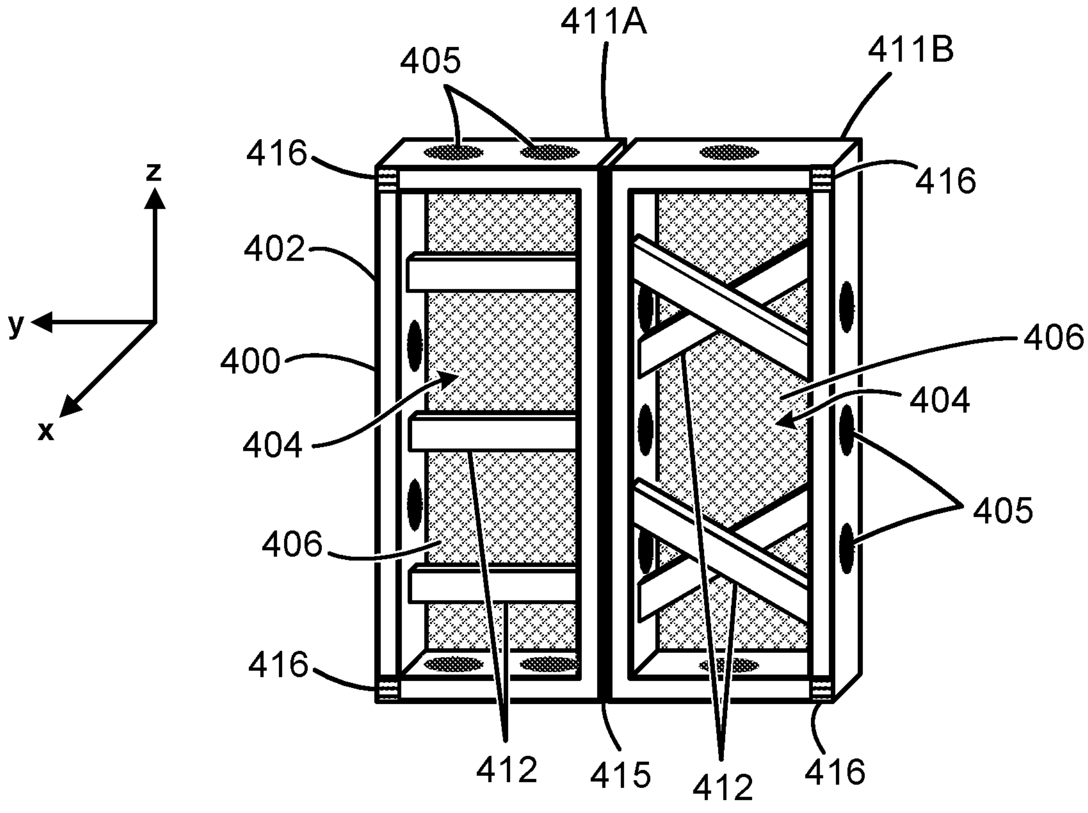
FIGS. 15A-B illustrate an example embodiment of an airflow device.
Figure 15B:
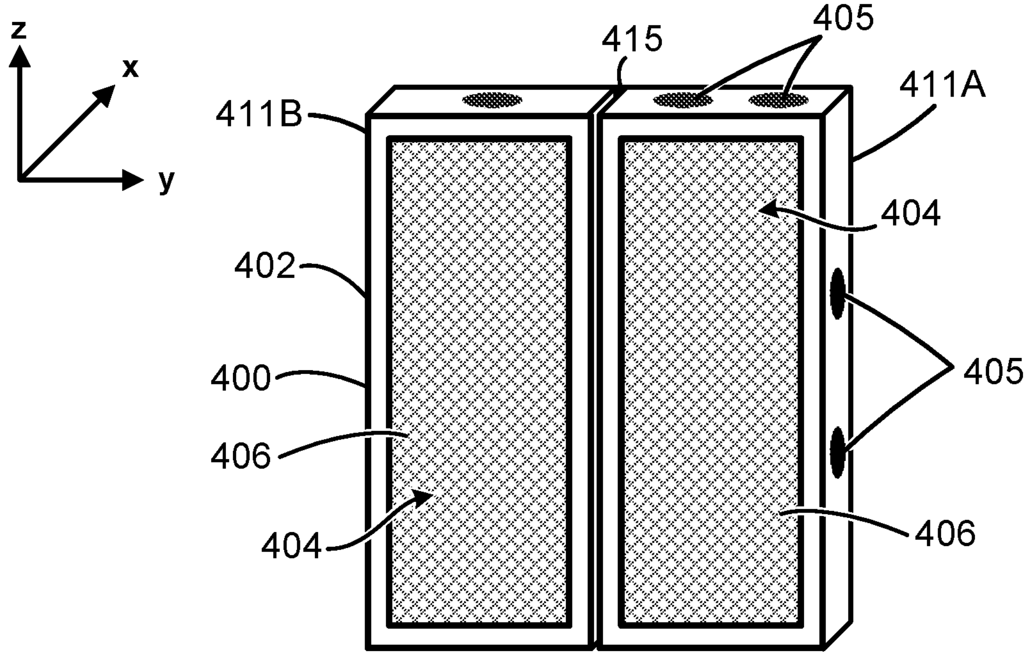

FIG. 13B illustrates a view of an end surface of an example embodiment of an airflow device 400 in the folded configuration. The frames 411 are similar to the frames in FIGS. 12A-C. However, in this embodiment, the frames 411 have three different widths: One frame 411B is wider than all the others, one frame 411C is narrower than all the others, and two frames 411A, D have widths that are identical to each other. Thus, the airflow device 400 has a different folded configuration than the airflow device 400 in FIGS. 12A-C, as well as the airflow device 400 in FIG. 13A. Also, in this embodiment, the frames 411 include peripheral openings 405 on their narrower sides (in some embodiments the frames 411 include peripheral openings 405 on one or more of their wider sides, for example as shown in FIGS. 15A-B). The peripheral openings 405 may improve the flow of air along the z axis (and along the y axis in embodiments that include peripheral openings 405 on one or more of their wider sides). And the configuration of the peripheral openings 405 may vary between the frames 411 or be identical.

Figure 13C:
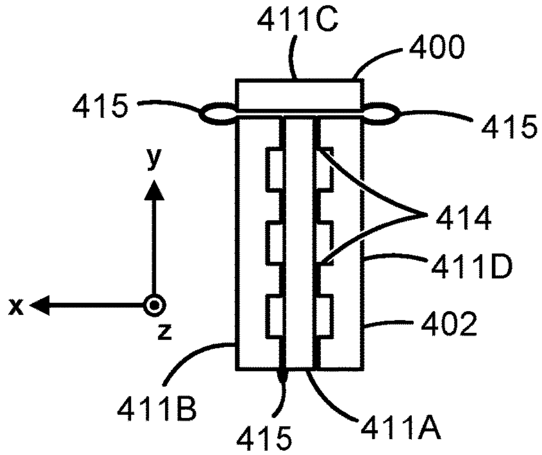
FIG. 13C illustrates a view of an end surface of an example embodiment of an airflow device in the folded configuration.

FIG. 13C illustrates a view of an end surface of an example embodiment of an airflow device 400 in the folded configuration. The frames 411 are similar to the frames in FIGS. 12A-C. However, in this embodiment, two of the frames 411B, D include protrusions 414.

Figure 13D:
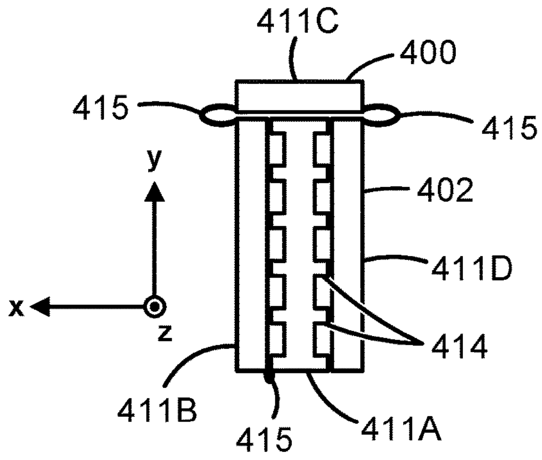
FIG. 13D illustrates a view of an end surface of an example embodiment of an airflow device in the folded configuration.

FIG. 13D illustrates a view of an end surface of an example embodiment of an airflow device in the folded configuration. The frames 411 are similar to the frames in FIGS. 12A-C. However, in this embodiment, one of the frames 411A includes protrusions 414. And some embodiments of the frames 411 include arrangements (locations, dimensions, quantities) of the protrusions 414 that are different from the arrangements of the protrusions 414 shown in FIGS. 13C-D.

Figure 13E:
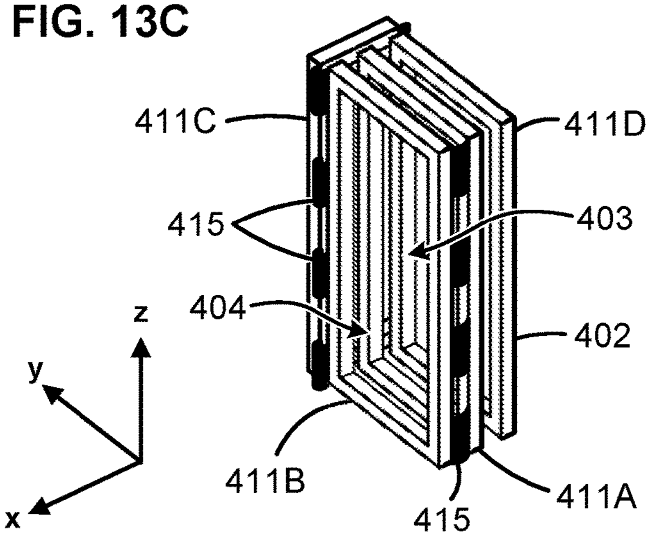
FIG. 13E illustrates a perspective view of an example embodiment of a foldable body.

FIG. 13E illustrates a perspective view of an example embodiment of a foldable body 402. The foldable body 402 is the same as the foldable body 402 from FIGS. 12A-B. However, no panels are attached to the foldable body 402. For example, the foldable body 402 may be used in an airflow device 400 that includes a casing that encloses the body 402.

Figure 14A:
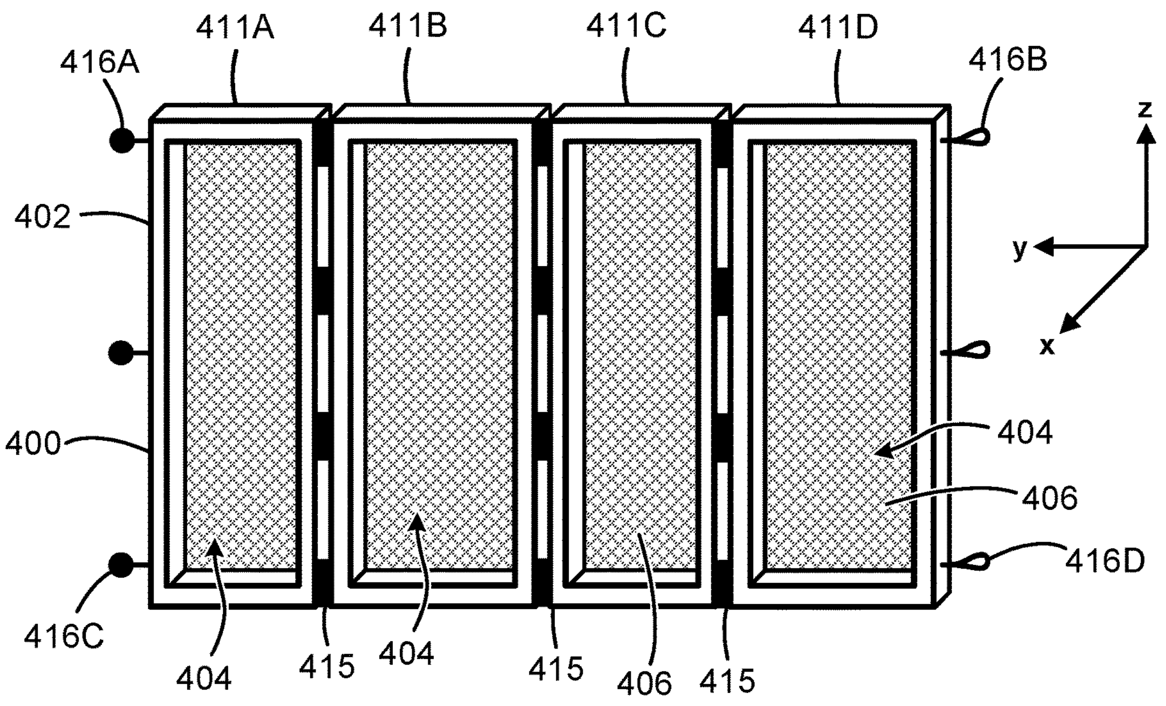
FIGS. 14A-B illustrate an example embodiment of an airflow device.
Figure 14B:
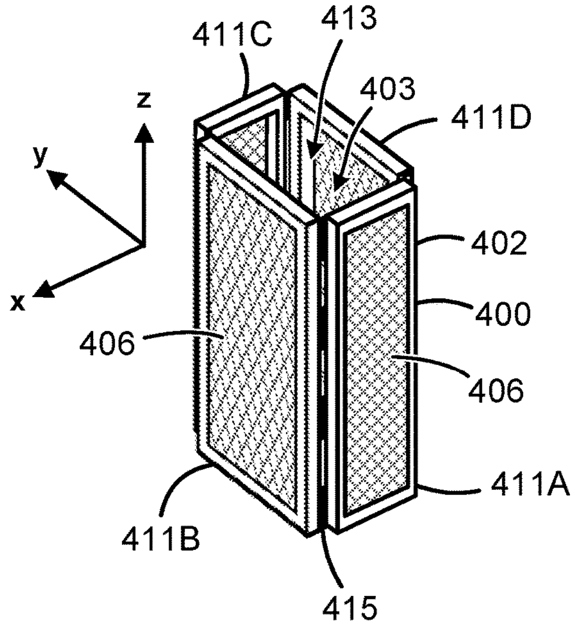

FIGS. 14A-B illustrate an example embodiment of an airflow device. FIG. 14A illustrates a perspective view of the airflow device 400 in the unfolded configuration, and FIG. 14B illustrates a perspective view of the airflow device 400 in the folded configuration.

The airflow device 400 includes a foldable body 402, which includes four frames 411 in this embodiment, and four breathable barriers, which may also be waterproof. In this embodiment, the four breathable barriers are panels 406. The frames 411 are similar to the frames 411 in FIGS. 12A-B. Like the frames 411 in FIGS. 12A-B, in some embodiments at least some of the frames 411 include one or more structures or one or more protrusions. Also, two of the frames 411A, D include fasteners 416, which can hold the airflow device 400 in the folded configuration. The fasteners 416 in this embodiment are bungee-cord ball-loop closures, although some embodiments use other fasteners.

Furthermore, two of the frames 411A, C have identical narrower widths, and two of the frames 411B, D have identical wider widths, the narrower widths being more narrow than the wider widths. When the body 402 is in the folded configuration, this gives the body 402 a rectangular cross section. Also, the fasteners 416 hold the frames 411 together such that the frames 411 form an air space 403 between them and such that the narrower ends have respective openings 413 that are surrounded by the frames 411.

Figure 14C:
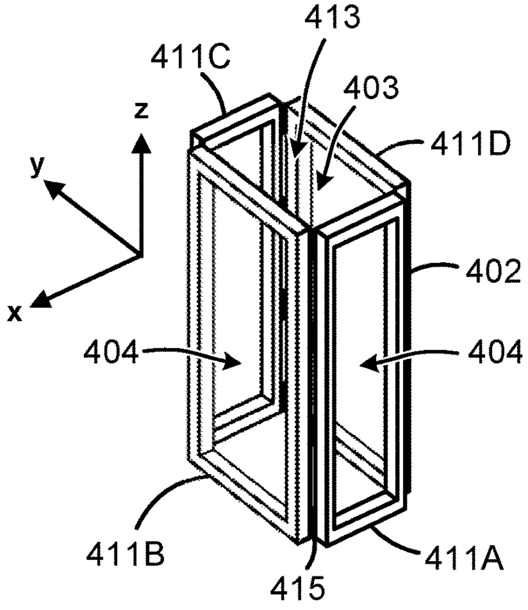
FIG. 14C illustrates a perspective view of an example embodiment of a foldable body.

FIG. 14C illustrates a perspective view of an example embodiment of a foldable body. The foldable body 402 is the same as the foldable body 402 from FIGS. 14A-B. However, no panels are attached to the foldable body 402. Additionally, for example, the foldable body 402 may be used in an airflow device 400 that includes a casing that encloses the body 402.

Figure 16A:
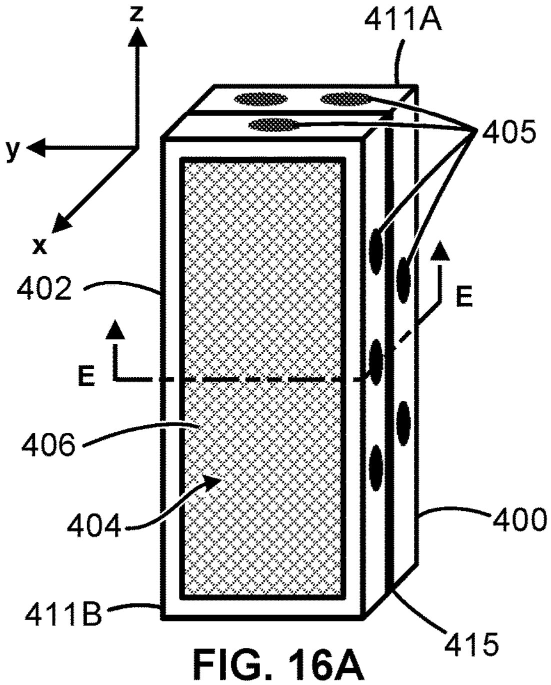
FIGS. 16A-C illustrate the airflow device from FIGS. 15A-B when the airflow device is in the closed position.
Figure 16B:
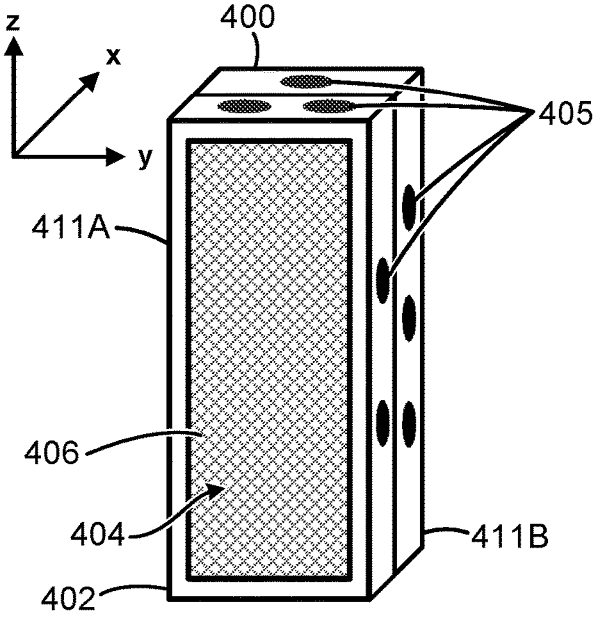
Figure 16C:
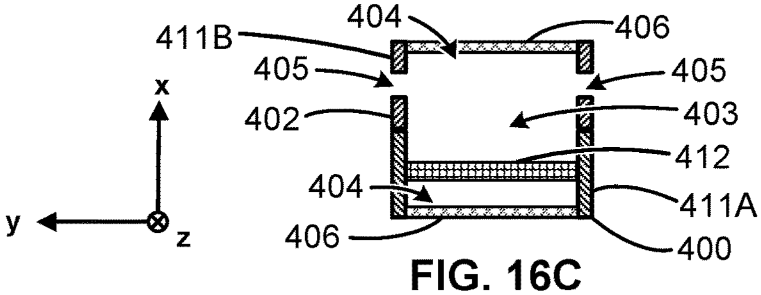

FIGS. 15A-B illustrate an example embodiment of an airflow device 400. And FIGS. 16A-C illustrate the example embodiment of the airflow device 400 from FIGS. 15A-B when the airflow device 400 is in the closed configuration. FIG. 15A shows a perspective view of the airflow device 400 from one viewpoint, and FIG. 15B shows a perspective view of the airflow device 400 from an opposite viewpoint. Likewise, FIG. 16A shows a perspective view of the airflow device 400 from one viewpoint, and FIG. 16B shows a perspective view of the airflow device 400 from an opposite viewpoint. Additionally, FIG. 16C illustrates a sectional view upon the plane that is indicated by line E-E in FIG. 16A.

The airflow device 400 includes a body 402 that includes two frames 411 and includes two or more breathable barriers, which may also be waterproof. In this embodiment, the frames 411 are thicker (i.e., longer along the x axis in FIGS. 15A-B) than the frames 411 in FIGS. 9A-B, 10A-C, and 11A-B. The frames 411 may be rigid or semi-rigid. The materials that compose the frames 411 may provide the frames 411 with some ability to compress and conform, which may increase patient comfort, while resisting compression past safety limits.

Also, the frames 411 include structures 412 that provide additional structural strength and that can be used to configure the rigidity of the frames 411 for a particular application. Furthermore, as shown in FIGS. 15A-B, the shapes and locations of the structures 412 may vary between the frames 411, which may improve the flow of air in one or more directions. And the shapes and locations of the structures 412 may be identical in both of the frames 411. The frames 411 include central openings 404.

The two or more breathable barriers are constituted by breathable panels 406, which may also be waterproof. The central openings 404 are covered by the panels 406, which also prevent tissue traversal through the central openings 404.

And each of the frames 411 includes peripheral openings 405 around its perimeter. The peripheral openings 405 may improve the flow of air along the y and z axes. And the configuration of the peripheral openings 405 may vary between the frames 411 or be identical. In FIGS. 15A-B, a first frame 411A has peripheral openings 405 that are in a different configuration than the configuration of the peripheral openings 405 of a second frame 411B.

The airflow device 400 further includes a hinge 415, which allows the frames 411 to be moved to a closed configuration. And the frames 411 include fasteners 416 that can hold the frames 411 in the closed configuration.

In FIGS. 16A-C, the second frame 411B has been swung over the first frame 411A. While the frames 411 are in the closed configuration, which is the position for patient use in an MRI procedure, the frames 411 and the structures 412 form an air space 403 that is in fluid communication with the central openings 404 and the peripheral openings 405.

Consequently, when the frames 411 are in the folded configuration, the frames 411, the structures 412, and the openings 404, 405 (*i*) create an air space 403 or a network of air spaces that are in fluid communication with each other and (ii) allow air to flow into, flow through, and flow out of the body 402 in any direction (to flow along the x, y, or z axes in FIGS. 16A-C). And, in the air space 403 or the network of air spaces, air can mix with air that entered the body 402 from a different direction. Furthermore, the panels 406 may prevent liquids and microorganisms from passing through the openings 404 to the air space 403 or the network of air spaces.

After the patient use is finished, the frames 411 can be moved to the unfolded configuration for easy cleaning and disinfection of all of their surfaces.

Furthermore, the airflow device 400 in FIGS. 15A-B and 16A-C may also include a port through which air can be injected by an external air supply.

Figure 16D:
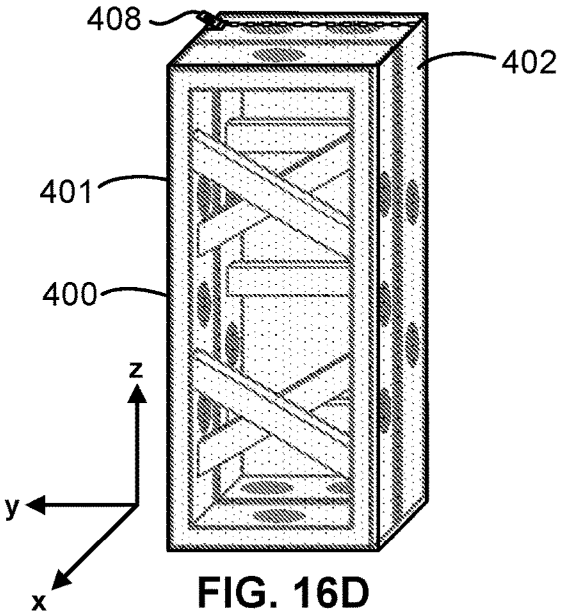
FIGS. 16D-E illustrate an example embodiment of an airflow device.
Figure 16E:
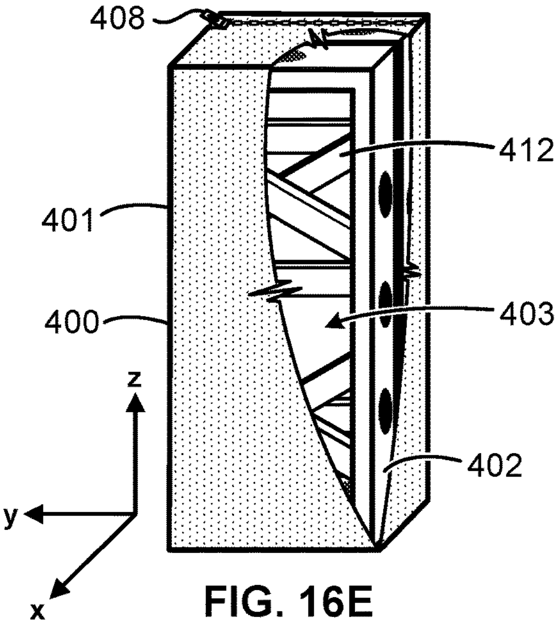

FIGS. 16D-E illustrate an example embodiment of an airflow device 400. The airflow device 400 includes the body 402 from FIGS. 15A-B and 16A-C. However, the one or more breathable barriers are constituted by a breathable casing 401 (which may also be waterproof) instead of panels 406. In FIG. 16D, to make the body 402 visible, the casing 401 is illustrated as being partially transparent. In FIG. 16E, the casing 401 is not illustrated as being transparent, but FIG. 16E illustrates a cutaway view through the casing 401.

Figure 17A:
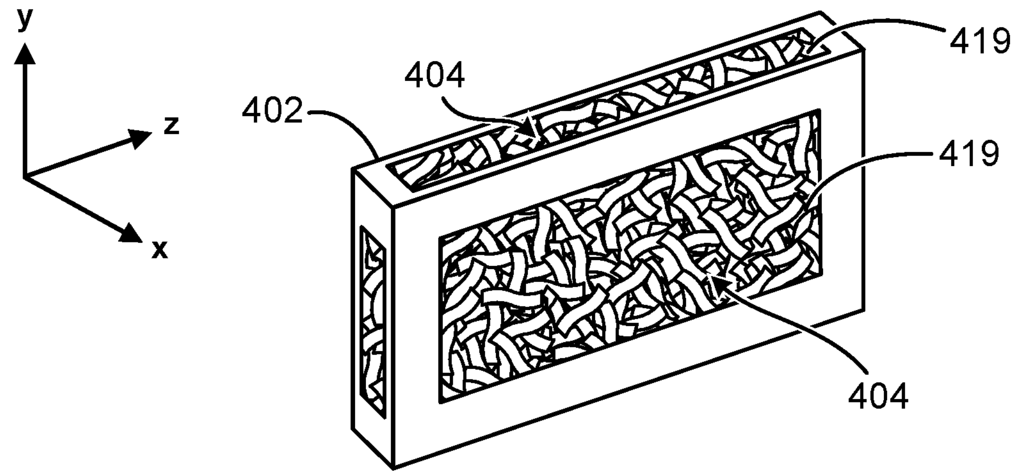
FIG. 17A illustrates an example embodiment of a body.

FIG. 17A illustrates an example embodiment of a body. In this embodiment, the body 402 includes a central cellular structure 419 and openings 404. The cellular structure 419 is porous and forms a network of openings and air spaces that are in fluid communication and that allow air to flow along at least two directions (along at least the x and z axes in FIG. 17A). The cellular structure 419 may be rigid or semi-rigid and may provide additional structural support. Also, the cellular structure 419 may be composed of multiple discrete components (e.g., multiple pieces of foam) that are adhered together. In FIG. 17A, the cellular structure 419 is visible through the openings 404.

Thus, the openings 404 and the cellular structure 419 form a network of air spaces that are in fluid communication with each other and allow air to flow into, flow through, and flow out of the body 402 in any direction (to flow along the x, y, or z axes in FIGS. 11A-B). And, in the network of air spaces, air can mix with air that entered the body 402 from a different direction.

Although the body 402 does not include a casing or any panels, the body 402 may be used as an airflow device. This may be particularly advantageous when the body 402 is composed of low-cost materials and can be economically discarded after use by one patient, which obviates any need to clean or disinfect the body 402 between uses.

Figure 17B:
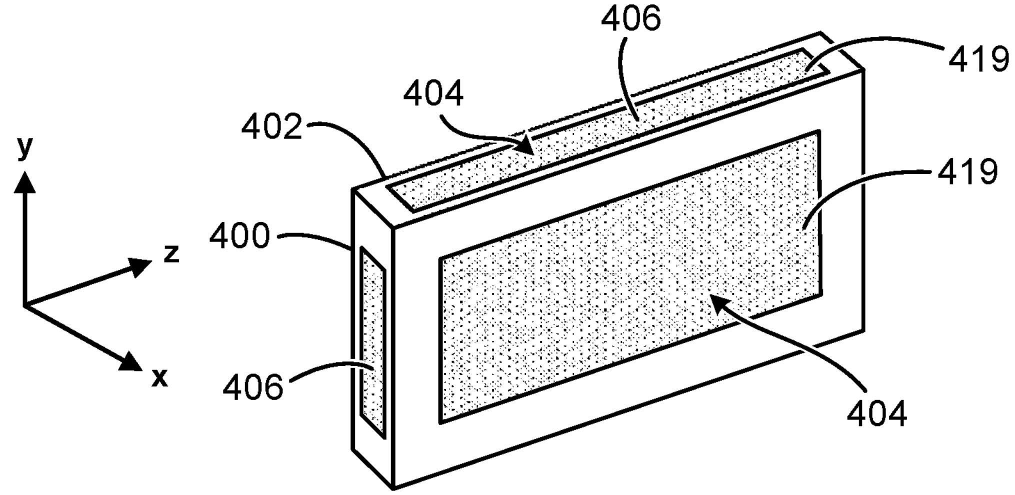
FIG. 17B illustrates an example embodiment of an airflow device that includes the body from FIG. 17A.

FIG. 17B illustrates an example embodiment of an airflow device 400. The airflow device 400 includes the body 402 from FIG. 17A and includes breathable panels 406 over the openings 404. The breathable panels 406, which may also be waterproof, constitute two or more breathable barriers.

Figure 18A:
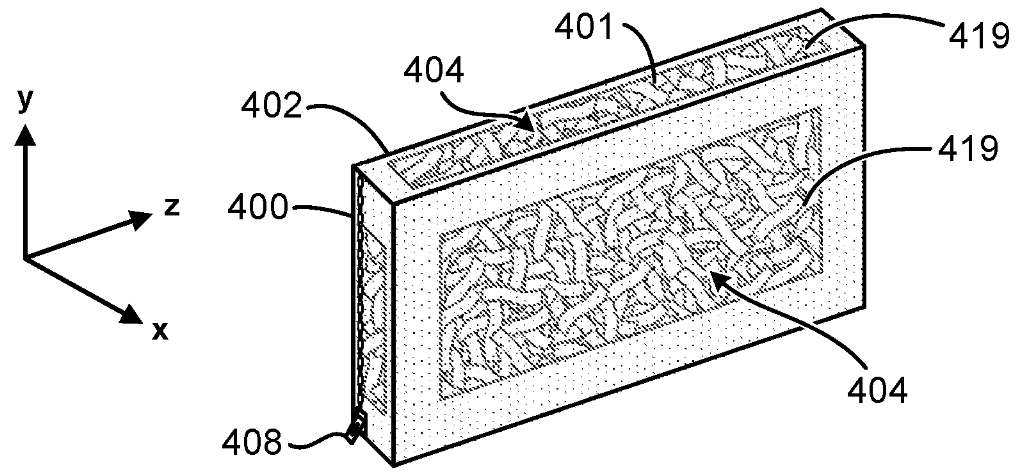
FIGS. 18A-B illustrates an example embodiment of an airflow device that includes the body from FIG. 17A.
Figure 18B:
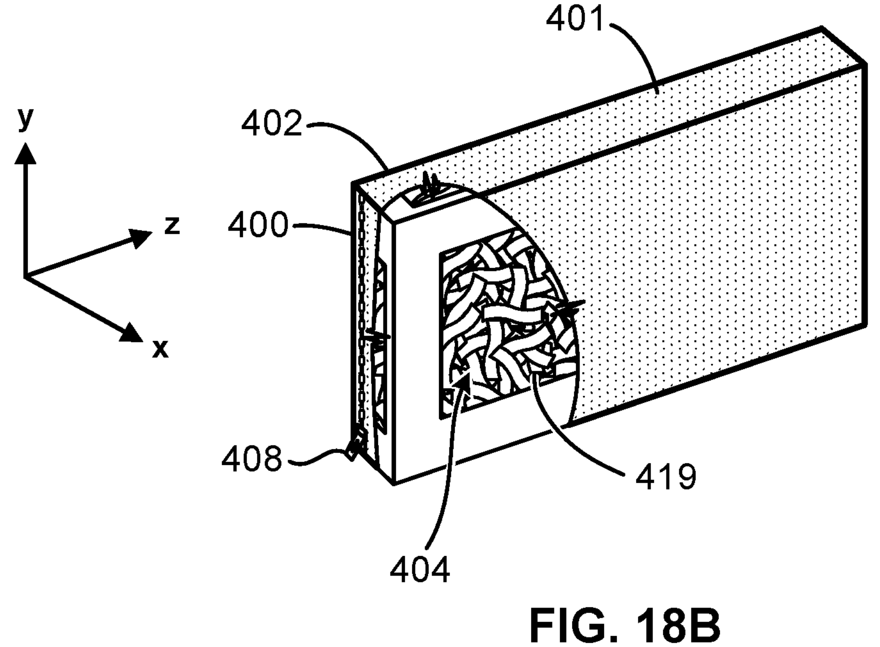

FIGS. 18A-B illustrate an example embodiment of an airflow device 400. The airflow device 400 includes the body 402 from FIG. 17A and a breathable casing 401 that encloses the body 402. The breathable casing 401, which may also be waterproof, constitutes a breathable barrier. And the casing 401 can be closed or opened by a zipper 408. In FIG. 18A, to make the body 402 visible, the casing 401 is illustrated as being partially transparent. In FIG. 18B, the casing 401 is not illustrated as being transparent, but FIG. 18B illustrates a cutaway view through the casing 401.

Figure 19A:
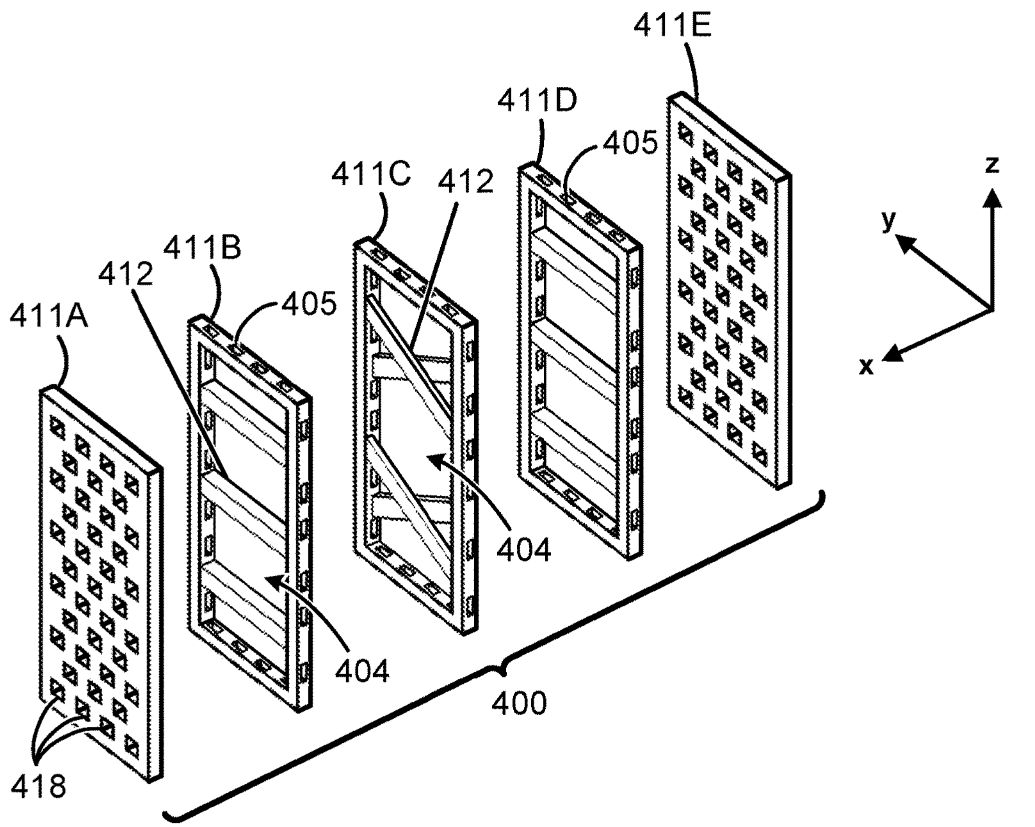
FIGS. 19A-B illustrate an example embodiment of an airflow device.
Figure 19B:
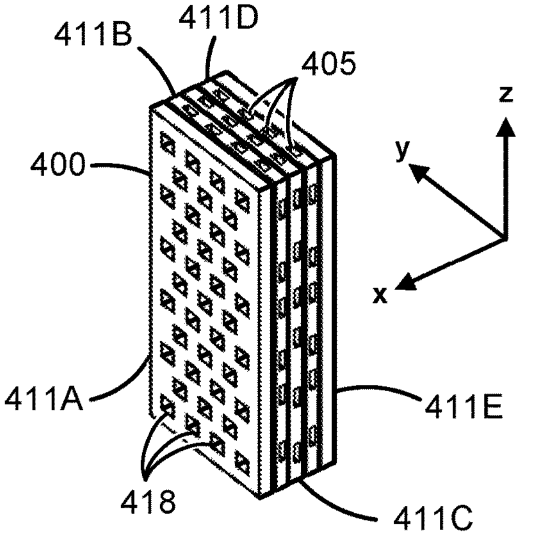

FIGS. 19A-B illustrate an example embodiment of an airflow device 400. FIG. 19A illustrates an exploded perspective view of the airflow device 400, and FIG. 19B illustrates a perspective view of the airflow device 400.

The airflow device 400 includes a plurality of frames 411 (five in this embodiment). Each of the end frames 411A, E includes a plurality of small openings 418 on its largest surface. Each of the three middle frames 411B-D forms an opening 404 and includes peripheral openings 405 around its perimeter. Also, each of the three middle frames 411B-D includes structures 412.

The frames 411 are joined together by adhesive or fasteners in this embodiment. In some embodiments, the frames 411 are joined by adhesives that are strong enough to prevent easy disassembly of the airflow device 400, but the airflow device 400 is composed of low-cost materials and can be economically discarded after use by one patient, which obviates any need to clean or disinfect the body 402 between uses. Also, in some embodiments, the frames 411 can be more easily disassembled for cleaning or disinfection.

When assembled, the frames 411, the openings 404, the peripheral openings 405, the structures 412, and the small openings 418 (*i*) form an air space or a network of air spaces that are in fluid communication with each other and (ii) allow air to flow into, flow through, and flow out of the airflow device 400 in any direction (to flow along the x, y, or z axes in FIGS. 19A-B). And, in the air space or the network of air spaces, air can mix with air that entered the airflow device 400 from a different direction.

Figure 19C:
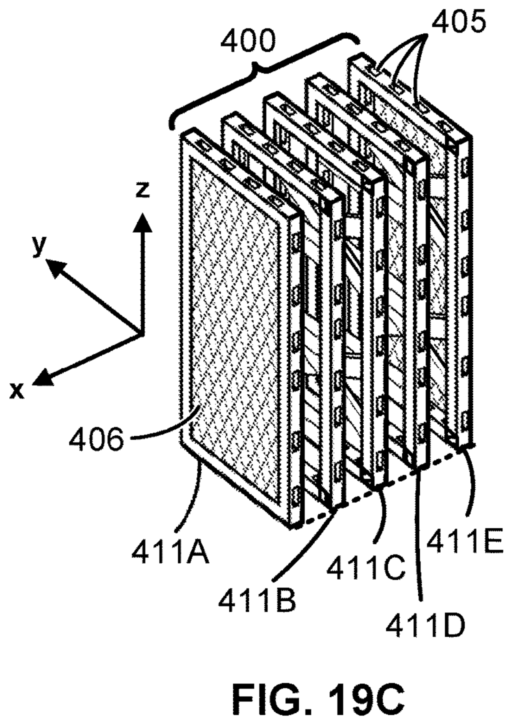
FIG. 19C illustrates an example embodiment of an airflow device.

FIG. 19C illustrates a perspective view of an example embodiment of an airflow device 400. This embodiment is similar to the embodiment in FIGS. 19A-B. However, instead of the small openings 418, the end frames 411A, E include larger openings (e.g., as shown by the end frames 411A, E in FIGS. 9A-B) and breathable barriers, which are constituted by breathable panels 406 (which may also be waterproof).

Figure 20A:
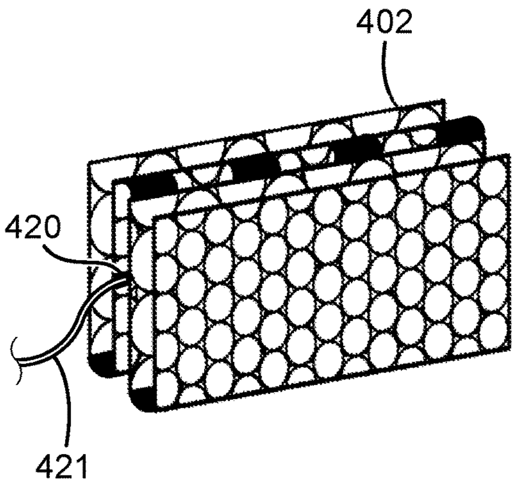
FIGS. 20A-E illustrate example embodiments of foldable bodies.

FIGS. 20A-E illustrate example embodiments of foldable bodies. The foldable body 402 in FIG. 20A is similar to the foldable body 402 in FIGS. 6A-B and 7A-B. However, the foldable body 402 in FIG. 20A includes a retaining structure 420 (e.g., clip, adhesive patch) that is configured to hold a hose 421, which may be supplied with air from an external air supply. Thus, the retaining structure 420 and the hose 421 allow the external air supply to supply air to the one or more air spaces in the body 402.

Figure 20B:
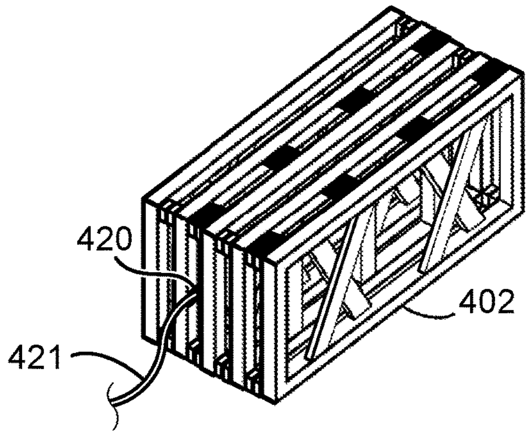

The foldable body 402 in FIG. 20B is similar to the foldable body 402 in FIGS. 9A-B and 10A-C. However, the foldable body 402 in FIG. 20B includes a retaining structure 420 (e.g., clip, adhesive patch) that is configured to hold a hose 421, which may be supplied with air from an external air supply. Thus, the retaining structure 420 and the hose 421 allow the external air supply to supply air to the one or more air spaces in the body 402.

Figure 20C:
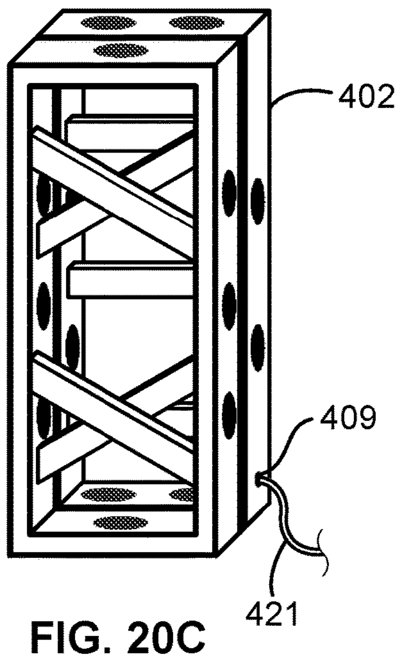

The foldable body 402 in FIG. 20C is similar to the foldable body 402 in FIGS. 15A-B and 16A-E. However, the foldable body 402 in FIG. 20C includes a port 409 that is configured to receive a hose 421, which may be supplied with air from an external air supply. The port 409 and the hose 421 allow the external air supply to supply air to the one or more air spaces in the body 402.

Figure 20D:
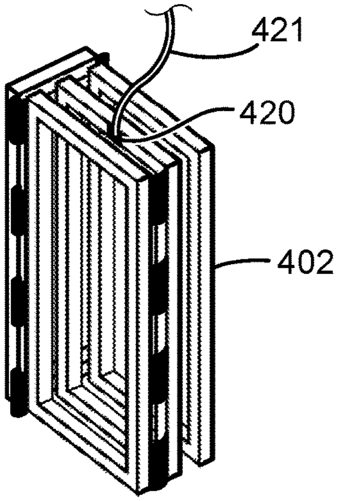

The foldable body 402 in FIG. 20D is similar to the foldable body 402 in FIGS. 12A-C and 13E. However, the foldable body 402 in FIG. 20D includes a retaining structure 420 (e.g., clip, adhesive patch) that is configured to hold a hose 421, which may be supplied with air from an external air supply. Thus, the retaining structure 420 and the hose 421 allow the external air supply to supply air to the one or more air spaces in the body 402.

Figure 20E:
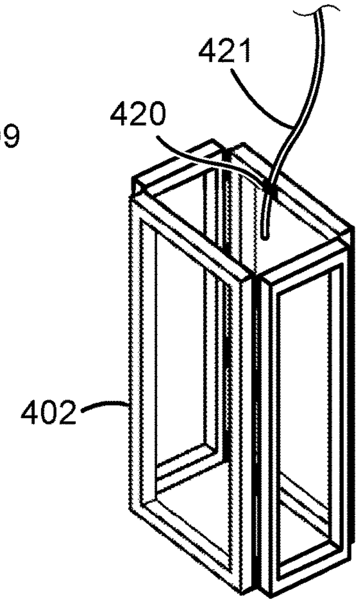

The foldable body 402 in FIG. 20E is similar to the foldable body 402 in FIGS. 14A-C. However, the foldable body 402 in FIG. 20E includes a retaining structure 420 (e.g., clip, adhesive patch) that is configured to hold a hose 421, which may be supplied with air from an external air supply. Thus, the retaining structure 420 and the hose 421 allow the external air supply to supply air to the one or more air spaces in the body 402.

Also, embodiments of airflow devices that include a body 402 that has a port 409 or a retaining structure 420 (e.g., as shown in FIGS. 20A-E) may also include a corresponding opening in a casing or a panel that is configured to receive the hose 421. This allows the air from the external air supply to be supplied through the casing or panel.

Figure 21:
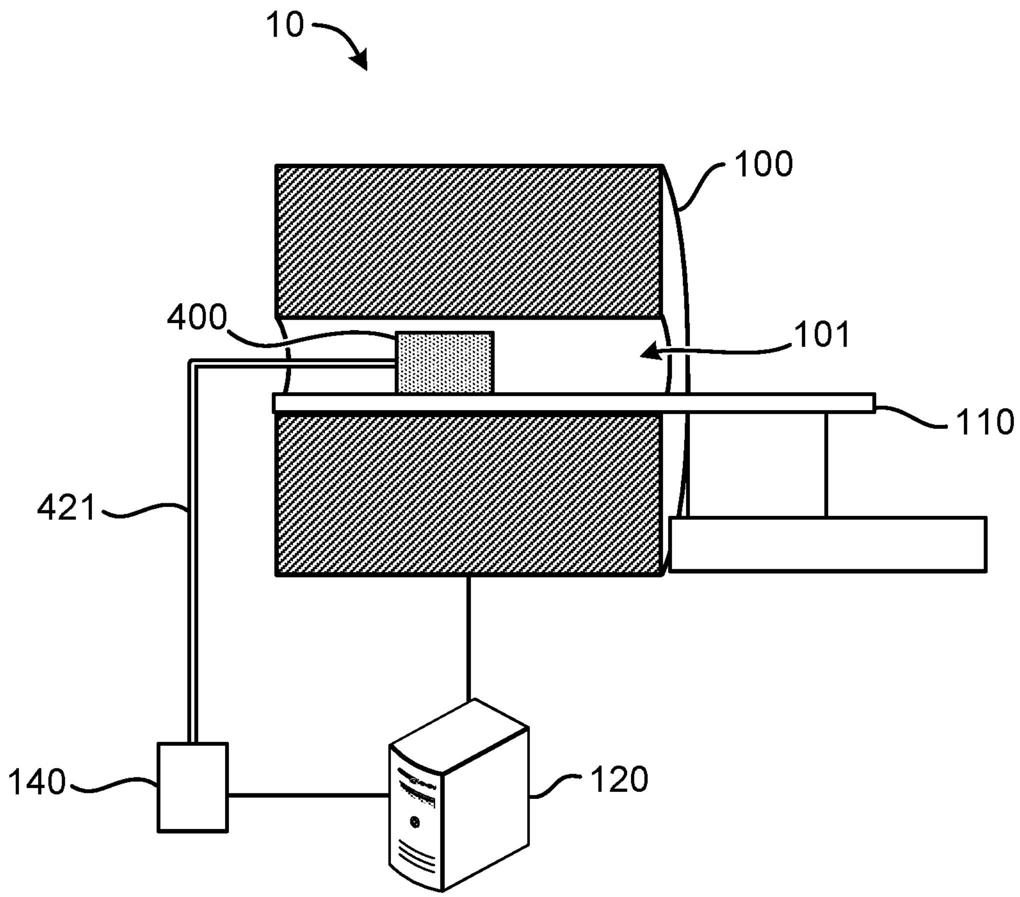
FIG. 21 illustrates an example embodiment of a medical-imaging system.

FIG. 21 illustrates an example embodiment of a medical-imaging system 10. The medical-imaging system 10 includes an MRI device 100, a system-control device 120, an air supply 140, and an airflow pad 400. Also, FIG. 21 illustrates a sectional view of the MRI device 100 upon the plane that is indicated by line A-A in FIG. 1.

The air supply 140 is connected to the airflow device 400 by a hose 421. Examples of the air supply 140 include the following: fans, pumps, compressors, and air tanks. Accordingly, the air supply 140 can supply air to the airflow device 400 via the hose 421.

The system-control device 120 controls the operations of the MRI device 100 and the air supply 140. For example, the system-control device 120 may activate or deactivate the air supply 140 (e.g., when the MRI device 100 is performing an MRI scan), and the system-control device 120 may control the volume of air or the pressure of the air that is supplied by the air supply 140.

Also, some embodiments of the MRI device 100 include the control device 120, the air supply 140, or both.

While certain embodiments have been described, these embodiments have been presented by way of example only and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Thus, the scope of the claims is not limited to the above-described embodiments and includes various modifications and equivalent arrangements.

The invention claimed is:

1. A device comprising:

a body that includes a plurality of openings and that forms one or more air spaces therein, wherein the plurality of openings and the one or more air spaces allow air to enter the body in a first direction, travel through the body in the first direction, exit the body in the first direction, enter the body in a second direction, travel through the body in the second direction, and exit the body in the second direction, wherein the first direction is orthogonal to the second direction, and wherein the body is inflatable; and one or more breathable barriers positioned over at least some of the plurality of openings, wherein the one or more breathable barriers allow air to flow through the at least some of the plurality of openings into the one or more air spaces, wherein the device is configured to position a patient in a bore of a magnetic-resonance-imaging device.

2. The device of claim 1, wherein each air space of the one or more air spaces is in direct or indirect fluid communication with each opening of the plurality of openings.

3. The device of claim 1, wherein the one or more air spaces allow air that passed through an opening, of the plurality of openings, in a first surface of the body to mix with air that entered through an opening, of the plurality of openings, in a second surface of the body that is orthogonal to the first surface.

4. The device of claim 1, wherein the one or more breathable barriers are also waterproof.

5. The device of claim 1, wherein the one or more breathable barriers are one or more breathable panels.

6. The device of claim 1, wherein the body is inflatable air that inflates the body does not mix with air that travels through the plurality of openings and the one or more air spaces.

7. The device of claim 1, wherein the body includes a chamber that holds air that inflates the body, and wherein, via the plurality of openings and the one or more air spaces, air can flow through the body without either entering or exiting the chamber.

8. The device of claim 7, further comprising:

an air reservoir, wherein air can travel between the air reservoir and the chamber, wherein air that travels from the air reservoir to the chamber inflates the body, and wherein the air reservoir and the chamber are a closed system.

9. A device comprising:

a breathable barrier; and a plurality of frames that are movable between an open configuration and a closed configuration, wherein, in the closed configuration, the plurality of frames form one or more air spaces and a plurality of openings, wherein, in the open configuration, the plurality of frames do not form the one or more air spaces, wherein the plurality of openings allow air to enter the one or more air spaces by traveling in a first direction, allow air to enter the one or more air spaces by traveling in a second direction, allow air to exit the one or more air spaces by traveling in the first direction, and allow air to exit the one or more air spaces by traveling in the second direction, wherein air can travel through the one or more air spaces in the first direction and in the second direction, wherein the first direction is orthogonal to the second direction, wherein at least one of the plurality of openings is covered by the breathable barrier, and wherein the device is configured to position a patient in a bore of a magnetic-resonance-imaging device.

10. The device of claim 9, wherein each frame of the plurality of frames includes at least one opening of the plurality of openings.

11. The device of claim 9, wherein at least one air space, of the one or more air spaces, is defined by both a first frame of the plurality of frames and a second frame of the plurality of frames.

12. The device of claim 11, wherein the breathable barrier abuts the at least one air space.

13. The device of claim 9, wherein the plurality of frames include a first frame and a second frame, wherein the one or more air spaces include an air space that is defined by both the first frame and the second frame, wherein the plurality of openings include a first opening through the first frame, wherein the plurality of openings include a second opening through the second frame, and wherein, by traveling in the first direction through the first opening and then through the second opening, air can enter and then exit the air space that is defined by both the first frame and the second frame without entering any other air space of the one or more air spaces.

14. The device of claim 9, further comprising:

one or more hinges, wherein each hinge of the one or more hinges joins two respective frames of the plurality of frames such that the plurality of frames can be changed from the open configuration to the closed configuration and from the closed configuration to the open configuration.

15. The device of claim 9, wherein each frame of the plurality of frames includes respective protrusions, and wherein the protrusions are configured to create openings between the plurality of frames when the plurality of frames are in the closed configuration.

16. The device of claim 9, further comprising a plurality of fasteners, wherein each frame of the plurality of frames includes at least part of a fastener of the plurality of fasteners, and wherein the plurality of fasteners are configured to hold the plurality of frames in the closed configuration.

17. A device comprising:

a breathable barrier, and a plurality of frames that form an air space and a plurality of openings, wherein the plurality of frames include a first frame and a second frame, wherein the first frame defines a first part of the air space, wherein the second frame defines a second part of the air space, wherein the plurality of openings allow air traveling in a first direction to enter and exit the air space, wherein the plurality of openings allow air traveling in a second direction to enter and exit the air space, wherein the first direction is orthogonal to the second direction, and wherein the breathable barrier covers at least one opening of the plurality of openings, and wherein the device is configured to position a patient in a bore of a magnetic-resonance-imaging device.

18. The device of claim 17, wherein the first frame has a first opening, of the plurality of openings, and a second opening, of the plurality of openings, wherein the second frame has a third opening, of the plurality of openings, and a fourth opening, of the plurality of openings, wherein the first opening and the second opening allow air to enter and exit the air space by traveling through the first frame, wherein the third opening and the fourth opening allow air to enter and exit the air space by traveling through the second frame, wherein the first opening and the third opening allow air traveling in the first direction to enter the air space and exit the air space, and wherein the second opening and the fourth opening allow air traveling in the second direction to enter the air space and exit the air space.

19. The device of claim 18, wherein the first frame has a fifth opening, of the plurality of openings, wherein the second frame has a sixth opening, of the plurality of openings, wherein the fifth opening and the sixth opening allow air traveling in a third direction to enter the air space and exit the air space, and wherein the third direction is orthogonal to both the first direction and the second direction.

20. The device of claim 17, wherein the breathable barrier is a breathable panel.

21. A system comprising:

a magnetic-resonance-imaging device that includes a bore;

an air supply;

a control device that is configured to control the air supply to supply air; and an airflow device that is connected to the air supply, wherein the airflow device is configured to fit inside the bore, and wherein the airflow device includes:

a breathable barrier, and a plurality of frames that are movable between an open configuration and a closed configuration, wherein, in the closed configuration, the plurality of frames form an air space and a plurality of openings, wherein the plurality of frames include a first frame and a second frame, wherein the first frame defines a first part of the air space, wherein the second frame defines a second part of the air space, wherein the plurality of openings allow air traveling in a first direction to enter and exit the air space, wherein the plurality of openings allow air traveling in a second direction to enter and exit the air space, wherein the first direction is orthogonal to the second direction, and wherein the breathable barrier covers at least one opening of the plurality of openings.

* * * * *